US008668909B2

(12) United States Patent
Kerschbaumer et al.

(10) Patent No.: US 8,668,909 B2
(45) Date of Patent: Mar. 11, 2014

(54) ANTI MIF ANTIBODIES

(75) Inventors: Randolf Kerschbaumer, Klosterneuburg (AT); Friedrich Scheiflinger, Vienna (AT); Manfred Rieger, Korneuburg (AT); Michael Thiele, Vienna (AT); Geert C. Mudde, Breitenfurt (AT); Juergen Muellberg, Lexington, MA (US); Rene Hoet, Zeist (NL)

(73) Assignees: Baxter International Inc., Deerfield, IL (US); Baxter Healthcare S.A., Glattpark (Opfikon) (CH); Dyax Corp., Cambridge, MA (US)

( * ) Notice: Subject to any disclaimer, the term of this patent is extended or adjusted under 35 U.S.C. 154(b) by 304 days.

(21) Appl. No.: 12/767,635

(22) Filed: Apr. 26, 2010

(65) Prior Publication Data

US 2010/0260768 A1    Oct. 14, 2010

Related U.S. Application Data

(63) Continuation of application No. 12/346,309, filed on Dec. 30, 2008, now abandoned.

(60) Provisional application No. 61/018,988, filed on Jan. 4, 2008, provisional application No. 61/094,685, filed on Sep. 5, 2008.

(51) Int. Cl.
| *A61K 39/395* | (2006.01) |
| *C12N 15/00* | (2006.01) |
| *C12N 5/07* | (2010.01) |
| *C07K 16/00* | (2006.01) |

(52) U.S. Cl.
USPC .......... 424/141.1; 424/133.1; 424/139.1; 424/130.1; 424/145.1; 424/158.1; 530/387.3; 530/388.1; 530/388.15; 530/388.23; 435/320.1; 435/69.1; 435/326; 435/335; 435/336; 536/23.53

(58) Field of Classification Search
None
See application file for complete search history.

(56) References Cited

U.S. PATENT DOCUMENTS

| 6,030,615 | A | 2/2000 | Bucala et al. |
| 6,645,493 | B1 | 11/2003 | Bucula et al. |
| 2003/0099653 | A1 | 5/2003 | Bucala et al. |
| 2003/0235584 | A1 | 12/2003 | Kloetzer et al. |
| 2004/0156848 | A1 | 8/2004 | Bucala et al. |

FOREIGN PATENT DOCUMENTS

| JP | 09077799 A | 3/1997 |
| RU | 2 236 251 C2 | 9/2004 |
| WO | WO 98/17314 A1 | 4/1998 |
| WO | WO 2007/134538 A1 | 11/2007 |

OTHER PUBLICATIONS

Shih, http://www.biocarta.com/pathfiles/h_LAIRPATHWAY.asp, accessed Sep. 20, 2013.*
Marzo-Ortega et al., 2003, Ann. Rheum. Dis. 62:74-76.*
Kekow et al., 2012, Biologics: Targets and Therapy 6:191-199.*
Gura, 1997, Science 278:1041-1042.*
Freshney (Culture of Animal Cells, A Manual of Basic Technique, Alan R. Liss, Inc., 1983, New York, p. 4).*
Dermer, 1994, Bio/Technology 12:320.*
Burmeister, G. et al., "Generation and Characterization of a Monoclonal Antibody (1C5) To Human Inhibitory Factor (MIF)," *Immunobiol.*, 1986, vol. 171, pp. 461-474.
Geczy, C.L. et al., "Production and Characterization of Antisera Against Human Macrophage Migration Inhibitory Factor (MIF)," *Molecular Immunology*, 1980, vol. 17, pp. 539-553.
Weiser, W.Y. et al., "Generation of Human Hybridomas Producing Migration Inhibitory Factor (MIF) and of Murine Hybridomas Secreting Monoclonal Antibodies to Human MIF," *Cellular Immunology*, 1985, vol. 90, pp. 167-178.
IPRP and Written Opinion issued Jul. 6, 2010 in PCT/EP2008/011146 (9 pages).
Calandra, Thierry et al.; "Macrophage Migration Inhibitory Factor: A Counter-Regulator of Glucocorticoid Action and Critical Mediator of Septic Shock"; 1996, *Journal of Inflammation*, vol. 47, pp. 39-51.
Chen, Zhiping et al.; "Evidence for a Role of Macrophage Migration Inhibitory Factor in Vascular Disease"; 2004, *Arteriosclerosis, Thrombosis, and Vascular Biology*, vol. 24, No. 4, pp. 709-714.
Cvetkovic, Ivana et al.; "Neutralization of macrophage migration inhibitory factor—novel approach for the treatment of immunoinflammatory disorders"; 2006, *International Immunophamacology*, vol. 6, pp. 1527-1534.
Galat, Andrzej et al.; A diversified family of 12-kDa proteins with a high amino acid sequence similarity to macrophage migration-inhibitory factor (MIF); 1994, *Eur. J. Biochem.*, vol. 224, pp. 417-421.
Kawaguchi, Tsutomu et al.; "A Monoclonal Antibody Against Migration Inhibitory Factor (MIF) Obtained by Immunization with MIF From the Human Lymphoblast Cell Line Mo"; 1986, *Journal of Leukocyte Biology*, vol. 39, pp. 223-232.
Leung, Joseph C.K. et al.; "Anti-macrophage migration inhibitory factor reduces transforming growth factor-β1 expression in experimental IgA nephropathy"; 2004, *Nephrol Dial Transplant*, vol. 19, pp. 1976-1985.

(Continued)

*Primary Examiner* — Elizabeth C Kemmerer
(74) *Attorney, Agent, or Firm* — Morgan, Lewis & Bockius LLP

(57) ABSTRACT

The present invention relates to monoclonal antibodies and antigen-binding portions thereof that specifically bind to the C-terminal or the center region of macrophage migration inhibitory factor (MIF). These anti-MIF antibodies and antigen-binding portions thereof further inhibit human MIF biological function. The invention also relates to isolated heavy and light chain immunoglobulins derived from anti-MIF antibodies and nucleic acid molecules encoding such immunoglobulins. The present invention also relates to a method of identifying anti-MIF antibodies, pharmaceutical compositions comprising these antibodies and a method of using these antibodies and compositions for the treatment of MIF-related conditions.

17 Claims, 14 Drawing Sheets

(56) References Cited

OTHER PUBLICATIONS

Meyer-Siegler, Katherine L. et al.; "Intraluminal Antibodies to Macrophage Migration Inhibitory Factor Decrease Substance P Induced Inflammatory Changes in the Rat Bladder and Prostate"; 2004, *The Journal of Urology*, vol. 172, pp. 1504-1509.

Meyer-Siegler, Katherine L. et al. "Inhibition of macrophage migration inhibitory factor decreases proliferation and cytokine expression in bladder cancer cells"; 2004, *BMC Cancer*, vol. 4, No. 1, 12 pages.

Ogawa, Hideaki et al.; "An Antibody for Macrophage Migration Inhibitory Factor Suppresses Tumour Growth and Inhibits Tumour-Associated Angiogenesis"; 2000, *Cytokine*, vol. 12, No. 4, pp. 309-314.

Rupreht, Ruth Rebeka et al.; "Murine monoclonal antibodies directed against human recombinant Macrophage Migration Inhibitory Factor"; 2000, *European Journal of Physiology*, vol. 440, No. 5, pp. R78-R80.

Shimizu, Tadamichi et al.; "Identification of macrophage migration inhibitory factor (MIF) in human skin and its immunohistochemical localization"; 1996, *FEBS Letters*, vol. 38, pp. 199-202.

Sumida, Yorihisa et al.; "Anti-Macrophage Migration Inhibitory Factor Antibody Suppresses Chronic Rejection of Heterotopically Transplanted Trachea in Rats"; 2006, *Acta Med.* vol. 51, pp. 51-56.

Watarai, Hiroshi et al.; "Posttranslational modification of the glycosylation inhibiting factor (GIF) gene product generates bioactive GIF"; 2000, *PNAS*, vol. 97, No. 24, pp. 13251-13256.

Weiser, Weishui Y. et al.; "Generation of Human Hybridomas Producing Migration Inhibitory Factor (MIF) and of Murine Hybridomas Secreting Monoclonal Antibodies to Human MIF"; 1985, *Cellular Immunology*, vol. 90, pp. 167-178.

Weiser, Weishui Y. et al.; "Molecular cloning of a cDNA encoding a human macrophage migration inhibitory factor"; 1989, *PNAS*, vol. 86, pp. 7522-7526.

Willis, Monte S. et al.; "Macrophage migration inhibitory factor mediates late cardiac dysfunction after burn injury"; 2005, *American Journal of Physiology: Heart and Circulatory Physiology*, vol. 288, No. 2, pp. H795-H804.

\* cited by examiner

Figure 1

| Name /SEQ ID No. | LV-FR1 | LV-CDR1 | LV-FR2 | LV-CDR2 | LV-FR3 | LV-CDR3 | LV-FR4 |
|---|---|---|---|---|---|---|---|
| Bax8 / SEQ ID No. 1 | DIQMTQSPSSLSASVGDRVTITC | RASQSISSYLN | WYQQKPGKAPKLLIY | AASSLQS | GVPSRFSGSGSGTDFTLTISSLQPEDFATYYC | QQSYSTPWT | FGQGTKVEIK |
| Bax69 / SEQ ID No. 2 | DIQMTQSPSSLSASVGDRVTITC | RSSQRIMTYLN | WYQQKPGKAPKLLIF | VASHSQS | GVPSRFRGSGSETDFTLTISGLQPEDSATYYC | QQSFWTPLT | FGGGTKVEIK |
| Bax74 / SEQ ID No. 3 | DIQMTQSPSSLPASVGDRVTITC | RASQSIGTYLS | WYQHKPGNAPKLLIY | ATSRLQS | GVPSRFSGGGSGTRFTLAISSLQPDDFATYFC | QQTYSTPLT | FGGGTKVDIK |
| Bax94 / SEQ ID No. 4 | DIQMTQSPGTLSLSPGERATLSC | RASQGVSSSSLA | WYQQKPGQAPRLLIY | GTSSRAT | GIPDRFSGSASGTDFTLTISRLQPEDFAVYYC | QQYGRSLT | FGGGTKVEIK |
| Bax152 / SEQ ID No. 5 | DIQMTQSPVTLSLSPGERATLSC | RASQSVRSSYLA | WYQQKPGQTPRLLIY | GASNRAT | GIPDRFSGSGSGTDFTLTISRLEPEDFAVYYC | QQYGNSLT | FGGGTKVEIK |
| BaxA10 / SEQ ID No. 6 | DIQMTQSPGTLSLSPGERATLSC | RASQGVSSSSLA | WYQQKPGQAPRLLIY | GTSSRAT | GIPDRFSGSASGTDFTLTISRLQPEDFAVYYC | QQYGRSLT | FGGGTKVEIK |

Figure 2

| Name / SEQ ID No. | HV-FR1 | HV-CDR1 | HV-FR2 | HV-CDR2 | HV-FR3 | HV-CDR3 | HV-FR4 |
|---|---|---|---|---|---|---|---|
| Bax8 / SEQ ID No. 7 | EVQLLESGGGLVQPGGSLRLSCAASGFTFS | IYTMD | WVRQAPGKGLEWVS | YISPSGGNTSYADSVKG | RFTISRDNSKNTLYLQMNSLRAEDTAVYYCAS | RQYVLRYFDWSADAFDI | WGQGTMVTVSS |
| Bax69 / SEQ ID No. 8 | EVQLLESGGGLVQPGGSLRLSCAASGFTFS | IYSMN | WVRQAPGKGLEWVS | SIGSSGGTTYYADSVKG | RFTISRDNSKNTLYLQMNSLRAEDTAVYYCAG | SQWLYGMDV | WGQGTTVTVSS |
| Bax74 / SEQ ID No. 9 | EVQLLESGGGLVQPGGSLRLSCAASGFTFS | KYYMI | WVRQAPGKGLEWVS | WIGPSGGFTFYADSVKG | RFTISRDNSKNTLYLQMNSLRAEDTAVYYCAR | GTPDYGGNSLDH | WGQGTLVTVSS |
| Bax94 / SEQ ID No. 10 | EVQLLESGGGLVQPGGSLRLSCAASGFTFS | IYAMD | WVRQAPGKGLEWVS | GIVPSGGFTKYADSVKG | RFTISRDNSKNTLYLQMNSLRAEDTAVYYCAR | VNVIAVAGTGYYYGMDV | WGQGTTVTVSS |
| Bax152 / SEQ ID No. 11 | EVQLLESGGGLVQPGGSLRLSCAASGFTFS | IYAMD | WVRQAPGKGLEWVS | GIVPSGGFTKYADSVKG | RFTISRDNSKNTLYLQMNSLRAEDTAVYYCAR | VNVIAVAGTGYYYGMDV | WGQGTTVTVSS |
| BaxA10 / SEQ ID No. 12 | EVQLLESGGGLVQPGGSLRLSCAASGFTFS | WYAMD | WVRQAPGKGLEWVS | GIVPSGGRTKYADSVKG | RFTISRDNSKNTLYLQMNSLRAEDTAVYYCAR | VNVIAVAGTGYYYGMDV | WGQGTTVTVSS |

Figure 3

Bax8: SEQ ID No. 13

```
       D   I   Q   M   T   Q   S   P   S   S   L   S   A   S   V   G   D   R   V   T
  1   GAC ATC CAG ATG ACC CAG TCT CCA TCC TCC CTG TCT GCA TCT GTA GGA GAC AGA GTC ACC
       I   T   C   R   A   S   Q   S   I   S   S   Y   L   N   W   Y   Q   Q   K   P
 61   ATC ACT TGC CGG GCA AGT CAG AGC ATT AGC AGC TAT TTA AAT TGG TAT CAG CAG AAA CCA
       G   K   A   P   K   L   L   I   Y   A   A   S   S   L   Q   S   G   V   P   S
121   GGG AAA GCC CCT AAG CTC CTG ATC TAT GCT GCA TCC AGT TTG CAA AGT GGG GTC CCA TCA
       R   F   S   G   S   G   S   G   T   D   F   T   L   T   I   S   S   L   Q   P
181   AGG TTC AGT GGC AGT GGA TCT GGG ACA GAT TTC ACT CTC ACC ATC AGC AGT CTG CAA CCT
       E   D   F   A   T   Y   Y   C   Q   Q   S   Y   S   T   P   W   T   F   G   Q
241   GAA GAT TTT GCA ACT TAC TAC TGT CAA CAG AGT TAC AGT ACC CCT TGG ACG TTC GGC CAA
       G   T   K   V   E   I   K
301   GGG ACC AAG GTG GAA ATC AAA
```

Bax69: SEQ ID N. 14

```
       D   I   Q   M   T   Q   S   P   S   S   L   S   A   S   V   G   D   R   V   T
  1   GAC ATC CAG ATG ACC CAG TCT CCA TCC TCC CTG TCT GCA TCT GTA GGA GAC AGA GTC ACC
       I   T   C   R   A   S   Q   R   I   M   T   Y   L   N   W   Y   Q   Q   K   P
 61   ATC ACT TGC CGG TCA AGT CAG AGA ATT ATG ACT TAT TTA AAT TGG TAT CAA CAA AAA CCG
       G   K   A   P   K   L   L   I   F   V   S   H   S   Q   S   G   V   P   S
121   GGG AAA GCC CCT AAA CTC CTG ATC TTT GTT TCA CAT TCA CAA AGT GGG GTC CCA TCC
       R   F   R   G   S   G   S   G   T   D   F   T   L   T   I   S   S   L   Q   P
181   AGG TTC AGA GGC AGT GGG TCT GGG ACA GAT TTC ACT CTC ACC ATC AGC AGT CTG CAA CCT
       E   D   S   A   T   Y   Y   C   Q   Q   S   F   W   T   P   L   T   F   G   G
241   GAA GAT TCT GCA ACT TAC TAC TGT CAA CAA AGT TTT TGG ACC CCC CTC ACT TTC GGC GGA
       G   T   K   V   E   I   K
301   GGG ACC AAG GTG GAG ATC AAA
```

Figure 3-con't

Bax74: SEQ ID No. 15

```
     D   I   Q   M   T   Q   S   P   S   S   L   P   A   S   V   G   D   R   V   T
  1  GAC ATC CAG ATG ACC CAG TCT CCA TCC TCC CTG CCT GCA TCT GTG GGA GAC AGA GTC ACC
     I   T   C   R   A   S   Q   S   I   G   T   Y   L   S   W   Y   Q   Q   K   P
 61  ATC ACT TGT CGG GCA AGT CAG AGC ATT GGT ACT TAT TTG AGT TGG TAT CAA CAC AAA CCG
     G   N   A   P   K   L   L   I   Y   A   T   S   R   L   Q   S   G   V   P   S
121  GGA AAT GCC CCC AAA CTC CTG ATC TAT GCT ACA TCT CGT TTG CAA AGT GGG GTC CCA TCG
     R   F   S   G   G   G   S   G   T   R   F   T   L   T   I   S   S   L   Q   P
181  AGG TTC AGT GGC GGT GGA TCT GGG ACA CGA TTC ACT CTC ACC ATC AGC AGT CTG CAA CCC
     D   D   F   A   T   Y   Y   C   Q   Q   T   Y   S   T   P   L   T   F   G   G
241  GAC GAT TTT GCA ACT TAC TAC TGT CAG CAG ACT TAC AGT ACC CCG CTC ACT TTC GGC GGA
     G   T   K   V   D   I   K
301  GGG ACC AAG GTG GAC ATC AAA
```

Bax94: SEQ ID No. 16

```
     D   I   Q   M   T   Q   S   P   G   T   L   S   L   S   P   G   E   R   A   T
  1  GAC ATC CAG ATG ACC CAG TCT CCA GGC ACC CTG TCT TTG TCT CCA GGG GAA AGA GCC ACC
     L   S   C   R   A   S   Q   S   V   G   V   L   I   Y   G   S   S   L   A   W   Y   Q   Q   K
 61  CTC TCC TGC AGG GCC AGT CAG AGT GTT CTC ATC TAC AGC AGC TTA GCC TGG TAC CAG AAA
     P   G   Q   A   P   R   L   L   I   Y   G   T   S   S   R   A   T   G   I   P
121  CCT GGC CAG GCT CCC AGG CTC CTC ATC TAT GGT ACA TCC AGC AGG GCC ACT GGC ATC CCA
     D   R   F   S   G   S   G   S   G   T   D   F   T   L   T   I   S   R   L   Q
181  GAC AGG TTC AGT GGC AGT GGG TCT GGG ACA GAC TTC ACT CTC ACC ATC AGC AGA CTG CAG
     P   E   D   F   A   V   Y   Y   C   Q   Q   Y   G   R   S   L   T   F   G   G
241  CCT GAA GAT TTT GCA GTG TAT TAC TGT CAG CAG TAT GGT AGG TCA CTC ACT TTC GGC GGA
     G   T   K   V   E   I   K
301  GGG ACC AAG GTG GAG ATC AAA
```

Figure 3-con't

Bax152: SEQ ID No. 17

```
  1  GAC ATC CAG ATG ACC CAG TCT CCA GTC ACC CTG TCT TTG TCT CCA GGG GAA AGA GCC ACC
      D   I   Q   M   T   Q   S   P   V   T   L   S   L   S   P   G   E   R   A   T
 61  CTC TCT TGC AGG GCC AGT CAG AGT GTT CGG AGT TAC TTA GCC TGG TAC CAG CAG AAA
      L   S   C   R   A   S   Q   S   V   R   S   Y   L   A   W   Y   Q   Q   K
121  CCC GGC CAG ACT CCC AGG CTC ATC TAT GGT GCC TCC AAC AGG GCC ATC GGC ATC CCA
      P   G   Q   T   P   R   L   I   Y   G   A   S   N   R   A   T   G   I   P
181  GAC AGG TTC AGT GGC AGT GGG TCT GGG ACA GAC TTC ACT CTC ACC ATC AGC AGA CTG GAG
      D   R   F   S   G   S   G   S   G   T   D   F   T   L   T   I   S   R   L   E
241  CCT GAA GAT TTT GCA GTC TAT TAC TGT CAG CAG TAT GGT AAC TCA CTC ACT TTC GGC GGA
      P   E   D   F   A   V   Y   Y   C   Q   Q   Y   G   N   S   L   T   F   G   G
301  GGG ACC AAG GTG GAG ATC AAA
      G   T   K   V   E   I   K
```

BaxA10: SEQ ID No. 18

```
  1  GAC ATC CAG ATG ACC CAG TCT CCA GGC ACC CTG TCT TTG TCT CCA GGG GAA AGA GCC ACC
      D   I   Q   M   T   Q   S   P   G   T   L   S   L   S   P   G   E   R   A   T
 61  CTC TCC TGC AGG GCC AGT CAG AGT GTT AGC AGC TAC TTA GCC TGG TAC CAG CAG AAA
      L   S   C   R   A   S   Q   S   V   S   S   Y   L   A   W   Y   Q   Q   K
121  CCT GGC CAG GCT CCC AGG CTC CTC ATC TAT GGT GCA TCC AGC AGG GCC ACT GGC ATC CCA
      P   G   Q   A   P   R   L   L   I   Y   G   A   S   S   R   A   T   G   I   P
181  GAC AGG TTC AGT GGC AGT GCG TCT GGG ACA GAC TTC ACT CTC ACC ATC AGC AGA CTG CAG
      D   R   F   S   G   S   A   S   G   T   D   F   T   L   T   I   S   R   L   Q
241  CCT GAA GAT TTT GCA GTG TAT TAC TGT CAG CAG TAT GGT AGG TCA CTC ACT TTC GGC GGA
      P   E   D   F   A   V   Y   Y   C   Q   Q   Y   G   R   S   L   T   F   G   G
301  GGG ACC AAG GTG GAG ATC AAA
      G   T   K   V   E   I   K
```

Figure 4

Bax8: SEQ ID No. 19

```
  1  GAA GTT CAA TTG TTA GAG TCT GGT GGC GGT CTT GTT CAG CCT GGT GGT TCT TTA CGT CTT
     E   V   Q   L   L   E   S   G   G   G   L   V   Q   P   G   G   S   L   R   L
 61  TCT TGC GCT GCT TCC GGA TTC ACT TTC ATT TAC TCT TAT ATG GAT TGG GTT CGC CAA GCT
     S   C   A   A   S   G   F   T   F   I   Y   S   Y   M   D   W   V   R   Q   A
121  CCT GGT AAA GGT TTG GAG TGG GTT GAG TCT TAT TCT CCT TCT GGT GGC AAT ACT TCT TAT
     P   G   K   G   L   E   W   V   E   S   Y   S   P   S   G   G   N   T   S   Y
181  GCT GAC TCC GTT AAA GGT CGC TTC ACT ATC TCT AGA GAC AAC TCT AAG AAT ACT CTC TAC
     A   D   S   V   K   G   R   F   T   I   S   R   D   N   S   K   N   T   L   Y
241  TTG CAG ATG AAC AGC TTA AGG GCT GAG GAC ACG GCC GTG TAT TAC TGT GCG AGT AGA CAA
     L   Q   M   N   S   L   R   A   E   D   T   A   V   Y   Y   C   A   S   R   Q
301  TAC GTA TTA CGA TAT TTT GAC TGG GCA GAT GCT TTT GAT ATC TGG GGC CAA GGG ACA
     Y   V   L   R   Y   F   D   W   A   D   A   F   D   I   W   G   Q   G   T
361  ATG GTC ACC GTC TCA AGC
     M   V   T   V   S   S
```

Bax69: SEQ ID No. 20

```
  1  GAA GTT CAA TTG TTA GAG TCT GGT GGC GGT CTT GTT CAG CCT GGT GGT TCT TTA CGT CTT
     E   V   Q   L   L   E   S   G   G   G   L   V   Q   P   G   G   S   L   R   L
 61  TCT TGC GCT GCT TCC GGA TTC ACT TTC ATT TAC TCT TAT ATG AAT TGG GTT CGC CAA GCT
     S   C   A   A   S   G   F   T   F   I   Y   S   Y   M   N   W   V   R   Q   A
121  CCT GGT AAA GGT TTG GAG TGG GTT TCT TCT ATC GGT GGC ACT ACT TAT TAT TAT TAT TAT
     P   G   K   G   L   E   W   V   S   S   I   G   G   T   T   Y   Y   Y   Y   Y
181  GCT GAC TCC GTT AAA GGT CGC TTC ACT ATC TCT AGA GAC AAC TCT AAG AAT ACT CTC TAC
     A   D   S   V   K   G   R   F   T   I   S   R   D   N   S   K   N   T   L   Y
241  TTG CAG ATG AAC AGC TTA AGG GCT GAG GAC ACG GCC GTG TAT TAC TGT GCG GGC TCA CAG
     L   Q   M   N   S   L   R   A   E   D   T   A   V   Y   Y   C   A   G   S   Q
301  TGG CTG TAC TAC ATG GAC GTC TGG GGC CAA GTC ACC GTC ACC GTC ACG GGC TCA AGC
     W   L   Y   Y   M   D   V   W   G   Q   V   T   V   T   V   T   G   S   S
```

Figure 4-con't

Bax74: SEQ ID No. 21

```
       E   V   Q   L   L   E   S   G   G   G   L   V   Q   P   G   G   S   L   R   L
  1   GAA GTT CAA TTG TTA GAG TCT GGT GGT GGC CTT GTT CAG CCT GGT GGT TCT TTA CGT CTT
       S   C   A   A   S   G   F   T   F   S   K   Y   Y   M   I   W   V   R   Q   A
 61   TCT TGC GCT GCT TCC GGA TTC ACT TTC TCT AAG TAC TAT ATG ATT TGG GTT CGC CAA GCT
       P   G   K   G   L   E   W   V   S   W   I   G   P   S   G   G   F   T   F   Y
121   CCT GGT AAA GGT TTG GAG TGG GTT TCT TGG ATC GGT CCT TCT GGT GGC TTT ACT TTT TAT
       A   D   S   V   K   G   R   F   T   I   S   R   D   N   S   K   N   T   L   Y
181   GCT GAC TCC GTT AAA GGT CGC TTC ACT ATC TCT AGA GAC AAC TCT AAG AAT ACT CTC TAC
       L   Q   M   N   S   L   R   A   E   D   T   A   V   Y   Y   C   A   R   G   T
241   TTG CAG ATG AAC AGC TTA AGG GCT GAG GAC ACG GCC GTG TAT TAC TGT GCG AGA GGG ACG
       P   D   Y   G   G   N   S   W   G   D   H   W   G   Q   G   T   L   V   T   S
301   CCC GAC TAC GGT GGT AAC TCC CTT GAC CAC TGG GGC CAG GGC ACC GTC ACC GTC TCA
       S
361   AGC
```

Bax94: SEQ ID No. 22

```
       E   V   Q   L   L   E   S   G   G   G   L   V   Q   P   G   G   S   L   R   L
  1   GAA GTT CAA TTG TTA GAG TCT GGT GGT GGC CTT GTT CAG CCT GGT GGT TCT TTA CGT CTT
       S   C   A   A   S   G   F   T   F   S   I   Y   A   M   D   W   V   R   Q   A
 61   TCT TGC GCT GCT TCC GGA TTC ACT TTC TCT ATT TAC GCT ATG GAT TGG GTT CGC CAA GCT
       P   G   K   G   L   E   W   V   S   G   I   V   P   S   G   G   F   T   K   Y
121   CCT GGT AAA GGT TTG GAG TGG GTT TCT GGT ATC GTT CCT TCT GGT GGC TTT ACT AAG TAT
       A   D   S   V   K   G   R   F   T   I   S   R   D   N   S   K   N   T   L   Y
181   GCT GAC TCC GTT AAA GGT CGC TTC ACT ATC TCT AGA GAC AAC TCT AAG AAT ACT CTC TAC
       L   Q   M   N   S   L   R   A   E   D   T   A   V   Y   Y   C   A   R   V   N
241   TTG CAG ATG AAC AGC TTA AGG GCT GAG GAC ACG GCC GTG TAT TAT TAC TGT GCG AGA GTG AAC
       V   I   A   V   A   G   T   G   Y   Y   Y   G   M   D   V   W   G   Q   G   G
301   GTT ATA GCA GTG GCT GGT ACT GGA TAC TAC TAC GGT ATG GAC GTC TGG GGC CAA GGG
       T   T   V   T   V   S   S
361   ACC ACG GTC ACC GTC TCA AGC
```

Figure 4-con't

Bax152: SEQ ID No. 23

```
  1  GAA GTT CAA TTG TTA GAG TCT GGT GGT CTT GTT CAG CCT GGT GGT TCT TTA CGT CTT
     E   V   Q   L   L   E   S   G   G   L   V   Q   P   G   G   S   L   R   L
 61  TCT TGC GCT GCT TCC GGA TTC ACT TTC TCT ATT TAC GCT ATG TGG GAT TGG GTT CGC CAA GCT
     S   C   A   A   S   G   F   T   F   S   I   Y   A   M   D   W   V   R   Q   A
121  CCT GGT AAA GGT TTG GAG TGG GTT TCT GGT ATC ATC TCT CCT GGT GGC TTT AAT ACT AAG TAT
     P   G   K   G   L   E   W   V   S   G   I   S   P   G   G   F   N   T   K   Y
181  GCT GAC TCC GTT CGC TTC ACT ATC TCT AGA GAC AAC TCT AAG AAT ACT CTC TAC
     A   D   S   V   R   F   T   I   S   R   D   N   S   K   N   T   L   Y
241  TTG CAG ATG AAC AGC TTA AGG GCT GAG GAC ACG GCC GTG TAT TAC TGT GCG AGA GTG CAA AAC
     L   Q   M   N   S   L   R   A   E   D   T   A   V   Y   Y   C   A   R   V   Q   N
301  GTT ATA GCA GTG GCT GGT ACT GGA TAC TAC TAC TAC TAC GGT ATG GAC GTC TGG GGC CAA GGG
     V   I   A   V   A   G   T   G   Y   Y   Y   Y   Y   G   M   D   V   W   G   Q   G
361  ACC ACG GTC ACC GTC TCA AGC
     T   T   V   T   V   S   S
```

BaxA10: SEQ ID No. 24

```
  1  GAA GTT CAA TTG TTA GAG TCT GGT GGT CTT GTT CAG CCT GGT GGT TCT TTA CGT CTT
     E   V   Q   L   L   E   S   G   G   L   V   Q   P   G   G   S   L   R   L
 61  TCT TGC GCT GCT TCC GGA TTC ACT TTC TCT TGG ATC TAC GCT ATG GAT TGG GTT CGC CAA GCT
     S   C   A   A   S   G   F   T   F   S   W   I   Y   A   M   D   W   V   R   Q   A
121  CCT GGT AAA GGT TTG GAG TGG GTT TCT GGT TAT ATC ATC TCT CCT GGT GGC CGT ACT AAG TAT
     P   G   K   G   L   E   W   V   S   G   Y   I   I   S   P   G   G   R   T   K   Y
181  GCT GAC TCC GTT CGC TTC ACT ATC TCT AGA GAC AAC TCT AAG AAT ACT CTC TAC
     A   D   S   V   R   F   T   I   S   R   D   N   S   K   N   T   L   Y
241  TTG CAG ATG AAC AGC TTA AGG GCT GAG GAC ACG GCC GTG TAT TAC TGT GCG AGA GTG CAA AAC
     L   Q   M   N   S   L   R   A   E   D   T   A   V   Y   Y   C   A   R   V   Q   N
301  GTT ATA GCA GTG GCT GGT ACT GGA TAC TAC TAC TAC TAC GGT ATG GAC GTC TGG GGC CAA GGG
     V   I   A   V   A   G   T   G   Y   Y   Y   Y   Y   G   M   D   V   W   G   Q   G
361  ACC ACG GTC ACC GTC TCA AGC
     T   T   V   T   V   S   S
```

Figure 8

| 1 | 2 | 3 | 4 | 5 | 6 | 7 |
|---|---|---|---|---|---|---|
| Antibody | Epitope | GCO IC50 (nM) | GCO max.Inh (%) | Proliferation Assay (P%) | Max competition with III.D.9 | Affinity (nM) |
| Bax8 | Center | 5 | 93 | 0.037 | 12% | nd |
| Bax69 | Center | 7 | 98 | 0.035 | 53% | 55 |
| Bax74 | C-terminus | 2 | 29 | 0.021 | 81% | 93 |
| Bax94 | C-terminus | 1 | 63 | 0.017 | 82% | 4 |
| Bax152 | C-terminus | 5 | 56 | 0.003 | 81% | 16 |
| BaxA10 | C-terminus | nd | nd | nd | nd | 0.4 |

SEQUENCE LISTING

<160> NUMBER OF SEQ ID NOS: 26

<210> SEQ ID NO 1
<211> LENGTH: 107
<212> TYPE: PRT
<213> ORGANISM: Artificial Sequence
<220> FEATURE:
<223> OTHER INFORMATION: anti macrophage migration inhibitory factor
      (MIF) monoclonal antibody Bax8 light chain variable region (V-L)

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: anti macrophage migration inhibitory factor
      (MIF) monoclonal antibody Bax69 light chain variable region (V-L)

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro

```
                65                  70                  75                  80
Glu Asp Ser Ala Thr Tyr Tyr Cys Gln Gln Ser Phe Trp Thr Pro Leu
                    85                  90                  95

Thr Phe Gly Gly Gly Thr Lys Val Glu Ile Lys
                100                 105
```

<210> SEQ ID NO 3
<211> LENGTH: 107
<212> TYPE: PRT
<213> ORGANISM: Artificial Sequence
<220> FEATURE:
<223> OTHER INFORMATION: anti macrophage migration inhibitory factor
      (MIF) monoclonal antibody Bax74 light chain variable region (V-L)

<400> SEQUENCE: 3

```
Asp Ile Gln Met Thr Gln Ser Pro Ser Ser Leu Pro Ala Ser Val Gly
1               5                   10                  15

Asp Arg Val Thr Ile Thr Cys Arg Ala Ser Gln Ser Ile Gly Thr Tyr
                20                  25                  30

Leu Ser Trp Tyr Gln His Lys Pro Gly Asn Ala Pro Lys Leu Leu Ile
            35                  40                  45

Tyr Ala Thr Ser Arg Leu Gln Ser Gly Val Pro Ser Arg Phe Ser Gly
        50                  55                  60

Gly Gly Ser Gly Thr Arg Phe Thr Leu Ala Ile Ser Ser Leu Gln Pro
65                  70                  75                  80

Asp Asp Phe Ala Thr Tyr Phe Cys Gln Gln Thr Tyr Ser Thr Pro Leu
                85                  90                  95

Thr Phe Gly Gly Gly Thr Lys Val Asp Ile Lys
                100                 105
```

<210> SEQ ID NO 4
<211> LENGTH: 107
<212> TYPE: PRT
<213> ORGANISM: Artificial Sequence
<220> FEATURE:
<223> OTHER INFORMATION: anti macrophage migration inhibitory factor
      (MIF) monoclonal antibody Bax94 light chain variable region (V-L)

<400> SEQUENCE: 4

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
                20                  25                  30

Ser Leu Ala Trp Tyr Gln Gln Lys Pro Gly Gln Ala Pro Arg Leu Leu
            35                  40                  45

Ile Tyr Gly Thr Ser Ser Arg Ala Thr Gly Ile Pro Asp Arg Phe Ser
        50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys
                100                 105
```

<210> SEQ ID NO 5
<211> LENGTH: 107
<212> TYPE: PRT
<213> ORGANISM: Artificial Sequence
<220> FEATURE:
<223> OTHER INFORMATION: anti macrophage migration inhibitory factor
      (MIF) monoclonal antibody Bax152 light chain variable region (V-L)

<400> SEQUENCE: 5

Asp Ile Gln Met Thr Gln Ser Pro Val Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Thr Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Leu
                85                  90                  95

Thr Phe Gly Gly Gly Thr Lys Val Glu Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: anti macrophage migration inhibitory factor
      (MIF) monoclonal antibody BaxA10 light chain variable region (V-L)

<400> SEQUENCE: 6

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys
            100                 105

<210> SEQ ID NO 7
<211> LENGTH: 126
<212> TYPE: PRT
<213> ORGANISM: Artificial Sequence
<220> FEATURE:
<223> OTHER INFORMATION: anti macrophage migration inhibitory factor
      (MIF) monoclonal antibody Bax8 heavy chain variable region (V-H)

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Thr Met Asp Trp Val Arg Gln Ala Pro Gly Lys Gly Leu Glu Trp Val
        35                  40                  45

Ser Tyr Ile Ser Pro Ser Gly Gly Asn Thr Ser Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Ser Arg Gln Tyr Val Leu Arg Tyr Phe Asp Trp Ser Ala Asp Ala
                    100                 105                 110

Phe Asp Ile Trp Gly Gln Gly Thr Met Val Thr Val Ser Ser
            115                 120                 125

<210> SEQ ID NO 8
<211> LENGTH: 118
<212> TYPE: PRT
<213> ORGANISM: Artificial Sequence
<220> FEATURE:
<223> OTHER INFORMATION: anti macrophage migration inhibitory factor
      (MIF) monoclonal antibody Bax69 heavy chain variable region (V-H)

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Ser Met Asn Trp Val Arg Gln Ala Pro Gly Lys Gly Leu Glu Trp Val
            35                  40                  45

Ser Ser Ile Gly Ser Ser Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Gln Trp Leu Tyr Gly Met Asp Val Trp Gly Gln Gly Thr
            100                 105                 110

Thr Val Thr Val Ser Ser
        115

<210> SEQ ID NO 9
<211> LENGTH: 121
<212> TYPE: PRT
<213> ORGANISM: Artificial Sequence
<220> FEATURE:
<223> OTHER INFORMATION: anti macrophage migration inhibitory factor
      (MIF) monoclonal antibody Bax74 heavy chain variable region (V-H)

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
                20                  25                  30

Tyr Met Ile Trp Val Arg Gln Ala Pro Gly Lys Gly Leu Glu Trp Val
            35                  40                  45

Ser Trp Ile Gly Pro Ser Gly Gly Phe Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Pro Asp Tyr Gly Gly Asn Ser Leu Asp His Trp Gly
            100                 105                 110

Gln Gly Thr Leu Val Thr Val Ser Ser
        115                 120
```

<210> SEQ ID NO 10
<211> LENGTH: 127
<212> TYPE: PRT
<213> ORGANISM: Artificial Sequence
<220> FEATURE:
<223> OTHER INFORMATION: anti macrophage migration inhibitory factor
      (MIF) monoclonal antibody Bax94 heavy chain variable region (V-H)

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser
        115                 120                 125

<210> SEQ ID NO 11
<211> LENGTH: 127
<212> TYPE: PRT
<213> ORGANISM: Artificial Sequence
<220> FEATURE:
<223> OTHER INFORMATION: anti macrophage migration inhibitory factor
      (MIF) monoclonal antibody Bax152 heavy chain variable region (V-H)

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser
        115                 120                 125

<210> SEQ ID NO 12
<211> LENGTH: 127
<212> TYPE: PRT
<213> ORGANISM: Artificial Sequence
<220> FEATURE:
<223> OTHER INFORMATION: anti macrophage migration inhibitory factor
      (MIF) monoclonal antibody BaxA10 heavy chain variable region (V-H)

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ala Met Asp Trp Val Arg Gln Ala Pro Gly Lys Gly Leu Glu Trp Val
        35                  40                  45

Ser Gly Ile Tyr Pro Ser Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser
        115                 120                 125

<210> SEQ ID NO 13
<211> LENGTH: 321
<212> TYPE: DNA
<213> ORGANISM: Artificial Sequence
<220> FEATURE:
<223> OTHER INFORMATION: anti macrophage migration inhibitory factor
      (MIF) monoclonal antibody Bax8 light chain variable region (V-L)

<400> SEQUENCE: 13
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccttggac gttcggccaa   300
gggaccaagg tggaaatcaa a                                             321

<210> SEQ ID NO 14
<211> LENGTH: 321
<212> TYPE: DNA
<213> ORGANISM: Artificial Sequence
<220> FEATURE:
<223> OTHER INFORMATION: anti macrophage migration inhibitory factor
      (MIF) monoclonal antibody Bax69 light chain variable region (V-L)

<400> SEQUENCE: 14
gacatccaga tgacccagtc tccatcctcc ctgtctgcat ctgtaggaga cagagtcacc    60
atcacttgcc ggtcaagtca gagaattatg acttatttaa attggtatca gcaaaaaccg   120
gggaaagccc ctaaactcct gatctttgtt gcatcccatt cacaaagtgg ggtcccatcc   180
aggttcagag gcagtgggtc tgagacagat ttcactctca ccatcagcgg tctgcaacct   240
gaagattctg caacttacta ctgtcaacaa agtttttgga ccccccctca tttcggcgga   300
gggaccaagg tggagatcaa a                                             321

<210> SEQ ID NO 15
<211> LENGTH: 321
<212> TYPE: DNA
<213> ORGANISM: Artificial Sequence
<220> FEATURE:
<223> OTHER INFORMATION: anti macrophage migration inhibitory factor
      (MIF) monoclonal antibody Bax74 light chain variable region (V-L)

<400> SEQUENCE: 15

```
gacatccaga tgacccagtc tccatcctcc ctgcctgcat ctgtgggaga cagagtcacc    60
atcacttgtc gggcaagtca gagcattggt acttatttga gttggtatca acacaaaccg   120
ggaaatgccc ccaaactcct gatctatgct acatctcgtt tgcaaagtgg cgtcccatcg   180
aggttcagtg gcggtggatc tgggacacga ttcactctcg ccatcagcag tctgcaaccc   240
gacgattttg caacttactt ctgtcagcag acttacagta ccccgctcac tttcggcgga   300
gggaccaagg tggacatcaa a                                             321
```

<210> SEQ ID NO 16
<211> LENGTH: 321
<212> TYPE: DNA
<213> ORGANISM: Artificial Sequence
<220> FEATURE:
<223> OTHER INFORMATION: anti macrophage migration inhibitory factor
      (MIF) monoclonal antibody Bax94 light chain variable region (V-L)

<400> SEQUENCE: 16

```
gacatccaga tgacccagtc tccaggcacc ctgtctttgt ctccagggga aagagccacc    60
ctctcctgca gggccagtca gggtgttagc agcagctcct tagcctggta ccagcagaaa   120
cctggccagg ctcccaggct cctcatctat ggtacatcca gcagggccac tggcatccca   180
gacaggttca gtggcagtgc gtctgggaca gacttcactc tcaccatcag cagactgcag   240
cctgaagatt ttgcagtgta ttactgtcag cagtatggta ggtcactcac tttcggcgga   300
gggaccaagg tggagatcaa a                                             321
```

<210> SEQ ID NO 17
<211> LENGTH: 321
<212> TYPE: DNA
<213> ORGANISM: Artificial Sequence
<220> FEATURE:
<223> OTHER INFORMATION: anti macrophage migration inhibitory factor
      (MIF) monoclonal antibody Bax152 light chain variable region (V-L)

<400> SEQUENCE: 17

```
gacatccaga tgacccagtc tccagtcacc ctgtctttgt ctccagggga aagagccacc    60
ctctcttgca gggccagtca gagtgttcgg agtagttact tagcctggta ccagcagaaa   120
cccggccaga ctcccaggct cctcatctat ggtgcctcca cagggccac tggcatccca    180
gacaggttca gtggcagtgg gtctgggaca gacttcactc tcaccatcag cagactggag   240
cctgaagatt ttgcagtcta ttactgtcag cagtatggta actcactcac tttcggcgga   300
gggaccaagg tggagatcaa a                                             321
```

<210> SEQ ID NO 18
<211> LENGTH: 321
<212> TYPE: DNA
<213> ORGANISM: Artificial Sequence
<220> FEATURE:
<223> OTHER INFORMATION: anti macrophage migration inhibitory factor
      (MIF) monoclonal antibody BaxA10 light chain variable region (V-L)

<400> SEQUENCE: 18

```
gacatccaga tgacccagtc tccaggcacc ctgtctttgt ctccagggga aagagccacc    60
ctctcctgca gggccagtca gggtgttagc agcagctcct tagcctggta ccagcagaaa   120
cctggccagg ctcccaggct cctcatctat ggtacatcca gcagggccac tggcatccca   180
gacaggttca gtggcagtgc gtctgggaca gacttcactc tcaccatcag cagactgcag   240
```

```
cctgaagatt ttgcagtgta ttactgtcag cagtatggta ggtcactcac tttcggcgga      300
gggaccaagg tggagatcaa a                                                321

<210> SEQ ID NO 19
<211> LENGTH: 378
<212> TYPE: DNA
<213> ORGANISM: Artificial Sequence
<220> FEATURE:
<223> OTHER INFORMATION: anti macrophage migration inhibitory factor
      (MIF) monoclonal antibody Bax8 heavy chain variable region (V-H)

<400> SEQUENCE: 19
gaagttcaat tgttagagtc tggtggcggt cttgttcagc ctggtggttc tttacgtctt      60
tcttgcgctg cttccggatt cactttctct atttacacta tggattgggt tcgccaagct     120
cctggtaaag gtttggagtg gtttcttat atctctcctt ctggtggcaa tacttcttat      180
gctgactccg ttaaaggtcg cttcactatc tctagagaca actctaagaa tactctctac     240
ttgcagatga acagcttaag ggctgaggac acggccgtgt attactgtgc gagtagacaa     300
tacgtattac gatattttga ctggtcggca gatgcttttg atatctgggg ccaagggaca     360
atggtcaccg tctcaagc                                                   378

<210> SEQ ID NO 20
<211> LENGTH: 354
<212> TYPE: DNA
<213> ORGANISM: Artificial Sequence
<220> FEATURE:
<223> OTHER INFORMATION: anti macrophage migration inhibitory factor
      (MIF) monoclonal antibody Bax69 heavy chain variable region (V-H)

<400> SEQUENCE: 20
gaagttcaat tgttagagtc tggtggcggt cttgttcagc ctggtggttc tttacgtctt      60
tcttgcgctg cttccggatt cactttctct atttactcta tgaattgggt tcgccaagct     120
cctggtaaag gtttggagtg gtttcttct atcggttctt ctggtggcac tacttattat      180
gctgactccg ttaaaggtcg cttcactatc tctagagaca actctaagaa tactctctac     240
ttgcagatga acagcttaag ggctgaggac acggccgtgt attactgtgc gggctcacag     300
tggctgtacg gtatggacgt ctggggccaa gggaccacgg tcaccgtctc aagc           354

<210> SEQ ID NO 21
<211> LENGTH: 363
<212> TYPE: DNA
<213> ORGANISM: Artificial Sequence
<220> FEATURE:
<223> OTHER INFORMATION: anti macrophage migration inhibitory factor
      (MIF) monoclonal antibody Bax74 heavy chain variable region (V-H)

<400> SEQUENCE: 21
gaagttcaat tgttagagtc tggtggcggt cttgttcagc ctggtggttc tttacgtctt      60
tcttgcgctg cttccggatt cactttctct aagtactata tgatttgggt tcgccaagct     120
cctggtaaag gtttggagtg gtttcttgg atcggtcctt ctggtggctt tactttttat      180
gctgactccg ttaaaggtcg cttcactatc tctagagaca actctaagaa tactctctac     240
ttgcagatga acagcttaag ggctgaggac acggccgtgt attactgtgc gagagggacg     300
cccgactacg gtggtaactc ccttgaccac tggggccagg gcaccctggt caccgtctca     360
agc                                                                   363

<210> SEQ ID NO 22
<211> LENGTH: 381
```

```
<212> TYPE: DNA
<213> ORGANISM: Artificial Sequence
<220> FEATURE:
<223> OTHER INFORMATION: anti macrophage migration inhibitory factor
      (MIF) monoclonal antibody Bax94 heavy chain variable region (V-H)

<400> SEQUENCE: 22
gaagttcaat tgttagagtc tggtggcggt cttgttcagc ctggtggttc tttacgtctt    60
tcttgcgctg cttccggatt cactttctct atttacgcta tggattgggt tcgccaagct   120
cctggtaaag gtttggagtg ggtttctggt atcgttcctt ctggtggctt tactaagtat   180
gctgactccg ttaaaggtcg cttcactatc tctagagaca actctaagaa tactctctac   240
ttgcagatga acagcttaag ggctgaggac acggccgtgt attactgtgc gagagtgaac   300
gttatagcag tggctggtac tgatactact actacggta tggacgtctg gggccaaggg    360
accacggtca ccgtctcaag c                                              381

<210> SEQ ID NO 23
<211> LENGTH: 381
<212> TYPE: DNA
<213> ORGANISM: Artificial Sequence
<220> FEATURE:
<223> OTHER INFORMATION: anti macrophage migration inhibitory factor
      (MIF) monoclonal antibody Bax152 heavy chain variable region (V-H)

<400> SEQUENCE: 23
gaagttcaat tgttagagtc tggtggcggt cttgttcagc ctggtggttc tttacgtctt    60
tcttgcgctg cttccggatt cactttctct atttacgcta tggattgggt cgccaagct    120 cctggtaaag gtttggagtg ggtttctggt atcgttcctt ctggtggctt tactaagtat   180
gctgactccg ttaaaggtcg cttcactatc tctagagaca actctaagaa tactctctac   240
ttgcagatga acagcttaag ggctgaggac acggccgtgt attactgtgc gagagtgaac   300
gttatagcag tggctggtac tgatactact actacggta tggacgtctg gggccaaggg    360
accacggtca ccgtctacag c                                              381

<210> SEQ ID NO 24
<211> LENGTH: 381
<212> TYPE: DNA
<213> ORGANISM: Artificial Sequence
<220> FEATURE:
<223> OTHER INFORMATION: anti macrophage migration inhibitoru factor
      (MIF) monoclonal antibody BaxA10 heavy chain variable region (V-H)

<400> SEQUENCE: 24
gaagttcaat tgttagagtc tggtggcggt cttgttcagc ctggtggttc tttacgtctt    60
tcttgcgctg cttccggatt cactttctct tggtacgcta tggattgggt tcgccaagct   120
cctggtaaag gtttggagtg ggtttctggt atctatcctt ctggtggccg tactaagtat   180
gctgactccg ttaaaggtcg cttcactatc tctagagaca actctaagaa tactctctac   240
ttgcagatga acagcttaag ggctgaggac acggccgtgt attactgtgc gagagtgaac   300
gttatagcag tggctggtac tgatactact actacggta tggacgtctg gggccaaggg    360
accacggtca ccgtctcaag c                                              381

<210> SEQ ID NO 25
<211> LENGTH: 4
<212> TYPE: PRT
<213> ORGANISM: Artificial Sequence
<220> FEATURE:
<223> OTHER INFORMATION: subsequence of Fc region of IgG4
```

```
<400> SEQUENCE: 25

Cys Pro Ser Cys
1

<210> SEQ ID NO 26
<211> LENGTH: 4
<212> TYPE: PRT
<213> ORGANISM: Artificial Sequence
<220> FEATURE:
<223> OTHER INFORMATION: sub-sequence of Fc region of IgG1

<400> SEQUENCE: 26

Cys Pro Pro Cys
1
```

ANTI MIF ANTIBODIES

CROSS-REFERENCE TO RELATED APPLICATIONS

This application is a continuation of U.S. application Ser. No. 12/346,309, now abandoned, filed Dec. 30, 2008, which claims benefit of U.S. provisional application No. 61/018,988, filed Jan. 4, 2008 and U.S. provisional application No. 61/094,685, filed Sep. 5, 2008. Each application is herein incorporated by reference.

FIELD OF THE INVENTION

The present invention relates to monoclonal antibodies and antigen-binding portions thereof that specifically bind to the C-terminal or the center region of macrophage migration inhibitory factor (MIF). These anti-MIF antibodies and antigen-binding portions thereof further inhibit human MIF biological function. The invention also relates to isolated heavy and light chain immunoglobulins derived from anti-MIF antibodies and nucleic acid molecules encoding such immunoglobulins. The present invention also relates to a method of identifying anti-MIF antibodies, pharmaceutical compositions comprising these antibodies and a method of using these antibodies and compositions for the treatment of MIF-related conditions.

BACKGROUND

Macrophage migration inhibitory factor (MIF) is a cytokine initially isolated based upon its ability to inhibit the in vitro random migration of macrophages (Bloom et al. Science 1966, 153, 80-2; David et al. PNAS 1966, 56, 72-7). Although MIF has been known since 1966 its precise function in the majority of cells is not known, but it seems that MIF is a critical upstream regulator of the innate and acquired immune response.

The human MIF cDNA was cloned in 1989 (Weiser et al., PNAS 1989, 86, 7522-6), and its genomic localization was mapped to chromosome 22. The product of the MIF gene is a amino acid protein of a molecular mass of 12.5 kDa. The protein is highly conserved with a sequence homology between human, mouse, rat, and bovine MIF between 90-96%. However, MIF has no significant sequence homology to any other protein. The three-dimensional structure of MIF is unlike any other cytokine or pituitary hormone. The protein crystallizes as a trimer of identical subunits. Each monomer contains two antiparallel alpha-helices that pack against a four-stranded beta-sheet. The monomer has an additional two beta-strands that interact with the beta-sheets of adjacent subunits to form the interface between monomers. The three beta-sheets are arranged to form a barrel containing a solvent-accessible channel that runs through the center of the protein along a molecular three-fold axis (Sun et al. PNAS 1996, 93, 5191-5196).

It was reported that MIF secretion from macrophages was induced at very low concentrations of glucocorticoid (Calandra et al. Nature 1995, 377, 68-71). However, as a proinflammatory cytokine, MIF also counter-regulates the effects of glucocorticoids and stimulates the secretion of other cytokines such as tumor necrosis factor TNF-α and interleukin IL-1β (Baugh et al, Crit. Care Med 2002, 30, S27-35) thus assuming a role in the pathogenesis of inflammatory and immune diseases. MIF is also directly associated with the growth of lymphoma, melanoma, and colon cancer (Nishihira et al. J Interferon Cytokine Res. 2000, 20:751-62).

MIF is a mediator of many pathologic conditions and thus associated with a variety of diseases including inflammatory bowel disease (IBD), rheumatoid arthritis (RA), acute respiratory distress syndrome (ARDS), asthma, glomerulonephritis, IgA nephropathy, cancer, myocardial infarct (MI), and sepsis.

Polyclonal and monoclonal anti-MIF antibodies have been developed against recombinant human MIF (Shimizu et al., FEBS Lett. 1996; 381, 199-202; Kawaguchi et al., J. Leukoc. Biol. 1986, 39, 223-232, and Weiser et al., Cell. Immunol. 1985, 90, 167-78).

Anti-MIF antibodies have been suggested for therapeutic use to inhibit TNF-α release. Calandra et al., (J. Inflamm. 1995. 47, 39-51) reportedly used anti-MIF antibodies to protect animals from experimentally induced gram-negative and gram-positive septic shock. Anti-MIF antibodies were suggested as a means of therapy to modulate cytokine production in septic shock and other inflammatory disease states.

U.S. Pat. No. 6,645,493 discloses monoclonal anti-MIF antibodies derived from hybridoma cells, which neutralize the biological activity of MIF. It could be shown in an animal model that these mouse derived anti-MIF antibodies had a beneficial effect in the treatment of endotoxin induced shock. Some of the described anti-MIF antibodies (III.D.9, XIV.14.3 and XIV.15.5) were used in the present invention for comparative experiments.

US 2003/0235584 discloses methods of preparing high affinity antibodies to MIF in animals in which the MIF gene has been homozygously knocked-out.

Glycosylation-inhibiting factor (GIF) is a protein described by Galat et al. (Eur. J. Biochem. 1994, 224, 417-21). MIF and GIF are now recognized to be identical. Watarai et al. (PNAS 2000, 97, 13251-6) described polyclonal antibodies binding to different GIF epitopes to identify the biochemical nature of the posttranslational modification of GIF in Ts cells. Watarai et al (PNAS 2000, 97, 13251-6) reported that GIF occurs in different conformational isoforms in vitro. One type of isomer occurs by chemical modification of a single cysteine residue. The chemical modification leads to conformational changes within the GIF protein and changes its biological function.

Given the complexity of involvement of MIF in various diseases an elucidation of the function of epitope-specific anti-MIF antibodies and its use for therapeutic approaches is highly desirable. Therefore, there exists a need for epitope-specific anti-MIF antibodies, which inhibit human MIF biological function for the treatment of diseases and conditions mediated by MIF.

SUMMARY OF THE INVENTION

The present invention relates to antibodies and antigen-binding portions thereof that specifically bind to the C-terminal or the center region of macrophage migration inhibitory factor (MIF).

The invention further relates to nucleic acid molecules encoding these antibodies or antigen-binding portions thereof, as well as to vectors comprising such a nucleic acid and to host cells comprising such a vector, as well as to methods for recombinant production of polypeptides encoded by nucleic acid molecules.

The invention also relates to pharmaceutical compositions comprising an anti-MIF antibody or an antigen-binding portion thereof. The pharmaceutical composition may also contain pharmaceutically acceptable carrier or other therapeutic agents.

The invention also relates to the use of an anti-MIF antibody or an antigen-binding portion thereof, in the manufacture of a medicament for the treatment of immunological diseases such as inflammatory diseases and hyperproliferative disorders.

The invention further relates to an anti-MIF antibody or antigen-binding portion thereof, for use in treating immunological diseases such as inflammatory diseases and hyperproliferative disorders.

The invention also relates to methods for treating a variety of immunological diseases and conditions, such as inflammatory diseases and hyperproliferative disorders with an effective amount of an anti-MIF antibody, or an antigen binding portion thereof.

The invention also relates to diagnostic methods. The anti-MIF antibody or antigen-binding portion thereof can be used to detect MIF in a biological sample.

The invention further relates to a process for the identification of an anti-MIF antibody capable of inhibiting active MIF and inducing a beneficial effect in an animal model.

BRIEF DESCRIPTION OF THE DRAWINGS

FIG. 1: shows the amino acid sequence of the light chain variable region of the human anti-MIF antibody of the invention FIG. 2: shows the amino acid sequence of the heavy chain variable region of the human anti-MIF antibody of the invention FIG. 3: shows the DNA sequences (SEQ ID NOs:13-18) and translations of the light chain variable region of human anti-MIF antibodies of the invention.

FIG. 4: shows the DNA sequences (SEQ ID NOs:19-24) and translation of the heavy chain variable region of human anti-MIF antibodies of the invention

FIG. 8: Table summarizing in-vitro properties of human anti-MIF antibodies.

DETAILED DESCRIPTION OF THE INVENTION

Definitions and General Techniques

Figure 5:
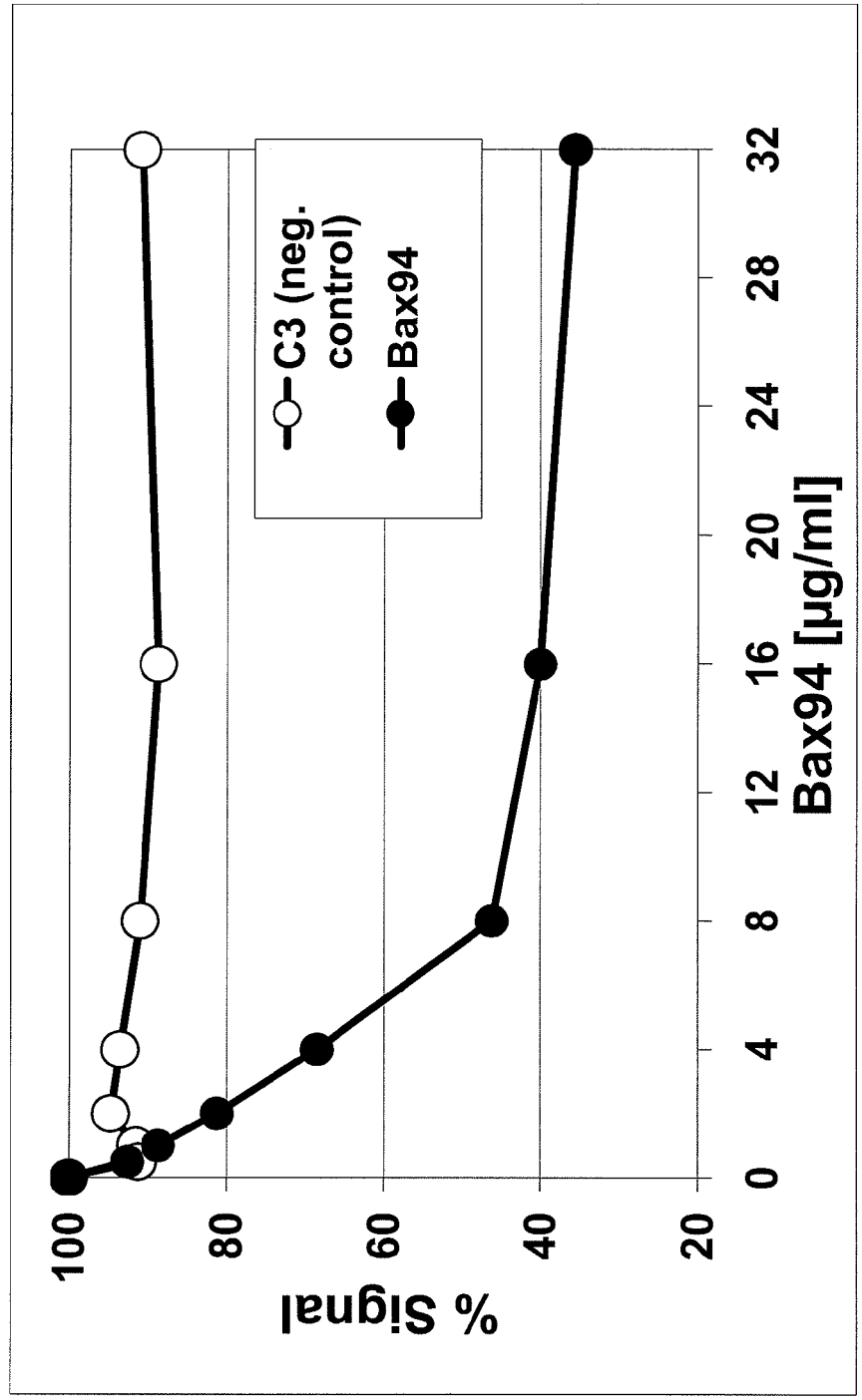
FIG. 5: Competition experiment of murine III.D.9 against a control antibody (C3) and anti-MIF antibody Bax94. A clear competition by increasing amounts of antibody Bax94 can be observed.

Unless otherwise defined herein, scientific and technical terms used in connection with the present invention shall have the meanings that are commonly understood by those of ordinary skill in the art. Generally, nomenclatures used in connection with, and techniques of, cell and tissue culture, molecular biology, immunology, microbiology, genetics and protein and nucleic acid chemistry described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual*, Cold Spring Harbor Laboratory Press, Cold Spring Harbor, N.Y. (1990), which are incorporated herein by reference.

"MIF" or "macrophage migration inhibitory factor" refers to the protein, which is known as a critical mediator in the immune and inflammatory response, especially as a counter-regulator of glucocorticoids. MIF includes mammalian MIF, specifically human MIF (Swiss-Prot primary accession number: P14174), wherein the monomeric form is encoded as a 115 amino acid protein but is produced as a 114 amino acid protein due to cleavage of the initial Methionine. "MIF" also includes "GIF" (glycosylation-inhibiting factor) and other forms of MIF such as fusion proteins of MIF. The numbering of the aminoacids of MIF starts with the N-terminal Methionine (amino acid 1) and ends with the C-terminal Alanine (amino acid 115).

The term "active MIF" refers to naturally occurring conformational isoforms of MIF, which are relevant for its biological function. Active MIF includes isoforms that can be observed on the surface of cells (such as THP1 or the like). Active MIF also includes MIF isoforms that occur in serum of mammals after challenge with bacteria.

An "antibody" refers to an intact antibody or an antigen-binding portion that competes with the intact antibody for specific binding. See generally, *Fundamental Immunology*, Ch. 7 (Paul, W., ed., 2nd ed. Raven Press, N.Y. (1989)) (incorporated by reference). The term antibody includes genetically engineered forms such as chimeric or humanized antibodies.

The term "antigen-binding portion" of an antibody refers to one or more fragments of an antibody that retain the ability to specifically bind to an antigen (e.g., MIF). Antigen-binding portions may be produced by recombinant DNA techniques or by enzymatic or chemical cleavage of intact antibodies. Antigen-binding portions include Fab, Fab', F(ab')$_2$, Fv, and complementarity determining region (CDR) fragments, single-chain antibodies (scFv), chimeric antibodies, diabodies and polypeptides that contain at least a portion of an antibody that is sufficient to confer specific antigen binding to the polypeptide. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia et. al. J. Mol. Biol. 196:901-917 (1987), or Chothia et al., Nature 342:878-883 (1989). An antibody or antigen-binding portion thereof can be derivatized or linked to another functional molecule (e.g., another peptide or protein). For example, an antibody or antigen-binding portion thereof can be functionally linked to one or more other molecular entities, such as another antibody (e.g., a bispecific antibody or a diabody), a detectable agent, a cytotoxic agent, a pharmaceutical agent, and/or a linking molecule.

The term "human antibody" refers to any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term encompasses such antibodies produced recombinantly in non-human cells, which might impart glycosylation not typical of human cells.

The term "humanized antibody" refers to immunoglobulins, immunoglobulin chains or fragments thereof (such as Fv, Fab, Fab', F(ab')$_2$, fragments, or other antigen-binding portions of antibodies), which contain sequences derived from a non-human immunoglobulin.

The term "chimeric antibody" refers to an antibody that comprises regions from two or more different species.

The term "isolated antibody" or "isolated antigen-binding portion thereof" refers to an antibody or an antigen-binding portion thereof that has been identified and selected from an antibody source such as a phage display library or a B-cell repertoire.

The term "$K_D$" refers to the equilibrium dissociation constant of a Fab portion of a particular antibody with the respective antigen.

The terms "center region" and "C-terminal region" of MIF refer to the region of human MIF comprising amino acids 35-68 and 86-115, respectively.

The term "epitope" includes any protein determinant capable of specific binding to an immunoglobulin or an antibody fragment. Epitopic determinants usually consist of chemically active surface groupings of molecules such as exposed amino acids, aminosugars, or other carbohydrate side chains and usually have specific three-dimensional structural characteristics, as well as specific charge characteristics.

The term "vector" refers to a nucleic acid molecule capable of transporting another nucleic acid to which it has been linked. In some embodiments, the vector is a plasmid, i.e., a circular double stranded DNA loop into which additional DNA segments may be ligated.

The term "host cell" refers to a cell line, which is capable to produce a recombinant protein after introducing an expression vector. The term "recombinant cell line", refers to a cell line into which a recombinant expression vector has been introduced. It should be understood that "recombinant cell line" means not only the particular subject cell line but also the progeny of such a cell line. Because certain modifications may occur in succeeding generations due to either mutation or environmental influences, such progeny may not, in fact, be identical to the parent cell, but are still included within the scope of the term "recombinant cell line" as used herein.

The term "pharmaceutically acceptable carrier" refers to any and all solvents, dispersion media, coatings, antibacterial and antifungal agents, isotonic and absorption delaying agents, and the like that are physiologically compatible.

Anti-MIF Antibodies

In one embodiment, the invention relates to isolated monoclonal antibodies or antigen-binding portions thereof, which specifically bind to the C-terminal or the center region of human MIF and further inhibit human MIF biological function. In some embodiments the monoclonal antibodies, are human monoclonal antibodies. In other embodiments the monoclonal antibodies, are humanized monoclonal antibodies.

In some embodiments, the light chain of the anti-MIF antibody comprises the amino acid sequence that is the same as the amino acid sequence of the $V_L$ of antibody Bax8 (SEQ ID NO: 1), antibody Bax69 (SEQ ID NO: 2), antibody Bax74 (SEQ ID NO: 3), antibody Bax94 (SEQ ID NO: 4), antibody Bax152 (SEQ ID NO: 5), antibody BaxA10 (SEQ ID NO: 6), or an amino acid sequence which has 85%, preferably 90% sequence homology to said amino acid sequences. In some embodiments, the light chain comprises the amino acid sequence from the beginning of the CDR1 to the end of the CDR3 of any one of said antibodies. In some embodiments, the light chain of the anti-MIF antibody comprises at least the light chain CDR1, CDR2 or CDR3 of the amino acid sequences shown in FIG. 1.

In some embodiments, the heavy chain comprises an amino acid sequence of the variable domain ($V_H$) of antibody Bax8 (SEQ ID NO: 7), antibody Bax69 (SEQ ID NO: 8), antibody Bax74 (SEQ. ID No: 9), antibody Bax94 (SEQ ID No: 10), antibody Bax152 (SEQ ID NO: 11), antibody Bax/A10 (SEQ ID NO: 12), or an amino acid sequence which has 85%, preferably 90% sequence homology to said amino acid sequences. In some embodiments, the heavy chain comprises the amino acid sequence from the beginning of the CDR1 to the end of the CDR3 of any one of said antibodies. In some embodiments, the heavy chain of the anti-MIF antibody comprises at least the heavy chain CDR1, CDR2 CDR3 of the amino acid sequences shown in FIG. 2.

Class and Subclass of Anti-MIF Antibodies

The anti-MIF antibody of the invention is an isolated monoclonal antibody. The anti-MIF antibody can be an IgG, IgM, IgE, an IgA, or an IgD molecule. In other embodiments, the anti-MIF antibody is an IgG and is an IgG1, IgG2, IgG3 or IgG4 subclass. In other embodiments, the antibody is either subclass IgG1 or IgG4. In other embodiments, the antibody is subclass IgG4. In some embodiments the IgG4 antibody has a single mutation changing the serine (serine228, according to the Kabat numbering scheme) to proline. Accordingly, the CPSC (SEQ ID NO: 25) sub-sequence in the Fc region of IgG4 becomes CPPC (SEQ ID NO: 26), which is a sub-sequence in IgG1 (Angal et al. Mol Immunol. 1993, 30, 105-108).

MIF Epitopes Recognized by Anti-MIF Antibodies

In some embodiments, the invention relates to anti-MIF antibodies or antigen-binding portions thereof that specifically bind to the regions spanning from amino acids 35-68 or 86-115 of human MIF, respectively, preferably the anti-MIF antibodies specifically bind to the regions spanning from amino acids 50 to 68, or 86 to 102, respectively, and inhibit human MIF biological function.

In other embodiments, the invention relates to anti-MIF antibodies, which specifically bind to active MIF and further inhibit human MIF biological function. In some embodiments, active MIF is membrane-bound.

It was surprisingly found that anti-MIF antibodies of the invention had the surprising property of competing anti-MIF antibody III.D.9 in binding studies with human MIF. Competition of III.D.9 can be determined as described in Example 5.

Binding Affinity of Anti-MIF Antibodies to Human MIF

The invention relates to anti-MIF antibodies or antigen-binding portions thereof, which bind to human MIF with a $K_D$ of $5 \times 10^{-7}$ M or less. In other embodiments, the antibodies bind to human MIF with a $K_D$ of $5 \times 10^{-8}$M or less, $5 \times 10^{-9}$M or less, or $5 \times 10^{-10}$ M or less.

The binding affinity of anti-MIF antibodies or antigen-binding portions thereof to human MIF can be determined by methods known in the art. The binding affinity for example can be measured by surface plasmon resonance (BIACORE). Example 10 exemplifies a method for determining affinity constants of anti-MIF antibodies by BIACORE technology.

In some embodiments, the invention further relates to anti-MIF antibodies or antigen-binding portions thereof, which bind to active MIF with a $K_D$ of less than 500 nM and further inhibit human MIF function biological function. In some embodiments, the anti-MIF antibodies or antigen-binding portions thereof bind active MIF with a $K_D$ of less than 50 nM.

Production of Anti-MIF Antibodies

Anti-MIF antibodies or antigen-binding portions thereof according to the present invention may be prepared by many methods known to the person skilled in the art, such as screening of phage display libraries of antibody fragments. Different formats of phage display libraries may be utilized, e.g. scFv or Fab fragments libraries or the like. A phage display library is screened for antibody fragments with desired affinities for certain MIF epitopes and the genetic material is recovered from the appropriate clone. In consecutive rounds of generating and screening libraries, antibody fragment can be isolated with an increased affinity compared to the affinity of the original antibody fragment isolated. The affinity of an identified anti-MIF fragment can be further enhanced by affinity maturation.

Nucleic Acids, Vectors, Host Cells, and Recombinant Methods of Making Anti-MIF Antibodies The invention further relates to nucleic acid molecules encoding anti-MIF antibodies or antigen-binding portions thereof according to the present invention, as well as to vectors comprising such nucleic acid and to host cells comprising such a vector, as well as to methods of recombinantly producing a polypeptide encoded by the nucleic acid molecule.

In some embodiments, the DNA sequence encoding the $V_L$ region of the anti-MIF antibody comprises the nucleotide sequence that is the same as the sequence of the $V_L$ of antibody Bax8 (SEQ ID NO: 13), antibody Bax69 (SEQ ID NO: 14), antibody Bax74 (SEQ ID NO: 15), antibody Bax94 (SEQ ID NO:16), antibody Bax152 (SEQ ID NO: 17), antibody BaxA10 (SEQ ID NO: 18) as shown in FIG. 3, or a sequence, which has 85%, preferably 90% sequence homology to any of said nucleotide sequences.

In some embodiments, the DNA sequence encoding the $V_H$ region of the anti-MIF antibody comprises the nucleotide sequence that is the same as the sequence of the $V_H$ of antibody Bax8 (SEQ ID NO: 19), antibody Bax69 (SEQ ID NO: 20), antibody Bax74 (SEQ ID NO: 21), antibody Bax94 (SEQ ID NO: 22), antibody Bax152 (SEQ ID NO: 23), antibody BaxA10 (SEQ ID NO: 24) as shown in FIG. 4, or a sequence, which has 85%, preferably 90% sequence homology to any of said nucleotide sequences.

The production of the anti-MIF antibodies according to the present invention include any method for the generation of recombinant DNA by genetic engineering, e.g. via reverse transcription of RNA and/or amplification of DNA and cloning into expression vectors.

In some embodiments, the vector is a viral vector, wherein additional DNA segments may be ligated into the viral genome. In some embodiments, the vector capable of autonomous replication in a host cell into which introduced (e.g., bacterial vectors having a bacterial origin of replication and episomal mammalian vectors). In other embodiments, the vector (e.g., non-episomal mammalian vectors) can be integrated into the genome of a host cell upon introduction into the host cell, and thereby replicated along with the host genome. Moreover, certain vectors are capable of directing the expression of genes to which they are operatively linked. Such vectors are referred to herein as "recombinant expression vectors" (or simply, "expression vectors").

Anti-MIF antibodies can be produced by means of conventional expression vectors, such as bacterial vectors (e.g., pBR322 and its derivatives), or eukaryotic vectors. Those sequences that encode the antibody can be provided with regulatory sequences that regulate the replication, expression and/or secretion from the host cell. These regulatory sequences comprise, for instance, promoters (e.g., CMV or SV40) and signal sequences. The expression vectors can also comprise selection and amplification markers, such as the dihydrofolate reductase gene (DHFR), hygromycin-B-phosphotransferase, and thymidine-kinase. The components of the vectors used, such as selection markers, replicons, enhancers, can either be commercially obtained or prepared by means of conventional methods. The vectors can be constructed for the expression in various cell cultures, e.g., in mammalian cells such as CHO, COS, HEK293, NS0, fibroblasts, insect cells, yeast or bacteria such as E. coli. In some instances, cells are used that allow for optimal glycosylation of the expressed protein.

The anti-MIF antibody light chain gene and the anti-MIF antibody heavy chain gene can be inserted into separate vectors or both genes are inserted into the same expression vector. The antibody genes are inserted into the expression vector by standard methods, e.g., ligation of complementary restriction sites on the antibody gene fragment and vector, or blunt end ligation if no restriction sites are present.

The production of anti-MIF antibodies or antigen-binding portions thereof may include any method known in the art for the introduction of recombinant DNA into eukaryotic cells by transfection, e.g. via electroporation or microinjection. For example, the recombinant expression of anti-MIF antibody can be achieved by introducing an expression plasmid containing the anti-MIF antibody encoding DNA sequence under the control of one or more regulating sequences such as a strong promoter, into a suitable host cell line by an appropriate transfection method resulting in cells having the introduced sequences stably integrated into the genome. The lipofection method is an example of a transfection method which may be used according to the present invention.

The production of anti-MIF antibodies may also include any method known in the art for the cultivation of said transformed cells, e.g. in a continuous or batchwise manner, and the expression of the anti-MIF antibody, e.g. constitutive or upon induction.

The host cell type according to the present invention may be any eukaryotic cell. In one embodiment the cell is a mammalian cell with the ability to perform posttranslational modifications of anti-MIF antibodies. For example said mammalian cell is derived from a mammalian cell line, like for example a cell line selected from the group consisting of SkHep-, CHO—, HEK293-, and BHK-cells. In one embodiment, the anti-MIF antibody is expressed in a DHFR-deficient CHO cell line, e.g., DXB11, and the addition of G418 as a selection marker. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Anti-MIF antibodies can be recovered from the culture medium using standard protein purification methods.

Additionally, the production of anti-MIF antibodies may include any method known in the art for the purification of an antibody, e.g. via anion exchange chromatography or affinity chromatography. In one embodiment the anti-MIF antibody can be purified from cell culture supernatants by size exclusion chromatography.

Properties of Anti-MIF Antibodies

The invention relates to anti-MIF antibodies or antigen-binding portion thereof, which possess at least one of the following properties:
  a) bind to the C-terminal or the center region of human MIF
  b) inhibit glucocorticoid overriding (GCO) activity,
  c) inhibit proliferation of cells lines such as fibroblasts or cancer cells (e.g. NIH/3T3 or PC-3)
  d) bind to active MIF
  e) does not bind to non-active MIF
  f) compete mouse anti-MIF antibody III.D.9.

In some embodiments, active MIF is an isoform of active MIF that occurs by treatment of human MIF with mild oxidizing reagents, such as Cystine or by immobilizing human MIF on a support such as an ELISA-plate or beads. In other embodiments, active MIF is an isoform of active MIF that occurs in vivo after challenge of animals with bacteria. In other embodiments, active MIF is an isoform of active MIF that occurs in vivo on the surface of cells (e.g. THP1, CFB).

In some embodiments, non-active MIF is reduced MIF (e.g. as described in Example 7) or, intracellular stored MIF.

In other embodiments, the anti-MIF antibodies or antigen-binding portion thereof bind active MIF with a $K_D$ less than 500 nM.

Pharmaceutical Compositions of Anti-MIF Antibodies and Methods of Treatment

The invention also relates to compositions comprising an anti-MIF antibody or an antigen-binding portion thereof, for the treatment of a subject in need of treatment for MIF-related conditions, specifically immunological diseases such as inflammatory diseases and hyperproliferative disorders.

In some embodiments, the subject in need of treatment is a human. Hyperproliferative disorders, such as cancerous diseases, that may be treated by anti-MIF antibodies of the invention can involve any tissue or organ and include but are not limited to brain, lung, squamous cell, bladder, gastric, pancreatic, breast, head, neck, liver, renal, ovarian, prostate, colorectal, esophageal, gynecological, nasopharynx, or thyroid cancers, melanomas, lymphomas, leukemias or multiple myelomas. In particular, anti-MIF antibodies of the invention are useful to treat carcinomas of the breast, prostate, colon and lung.

The invention also encompasses methods for the treatment of inflammatory diseases such as vasculitis, arthritis, sepsis, septic shock, endotoxic shock, toxic shock syndrome, acquired respiratory distress syndrome, glomerulonephritis, inflammatory bowel disease, Crohn's disease, ulcerative colitis, peritonitis, nephritis, atopic dermatitis, asthma, conjunctivitis, fever, Malaria or psoriasis in a subject, including a human, comprising the step of administering to said subject in need thereof a therapeutically effective amount of an anti-MIF antibody or antigen-binding portion thereof.

In other embodiments the composition comprising said anti-MIF antibody of the invention is used for the treatment of an inflammatory disease selected from the group consisting of glomerulonephritis, inflammatory bowel disease, nephritis and peritonitis.

The treatment may also involve administration of one or more anti-MIF antibody of the invention, or an antigen-binding fragment thereof, alone or with a pharmaceutically acceptable carrier. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The anti-MIF antibody of the invention and the pharmaceutical compositions comprising them, can be administered in combination with one or more other therapeutic, diagnostic or prophylactic agents. Additional therapeutic agents include other anti-neoplastic, anti-tumor, anti-angiogenic, chemotherapeutic agents or steroids, depending on the disease to be treated.

The pharmaceutical compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection. As will be appreciated by the skilled artisan, the route and/or mode of administration will vary depending upon the desired results.

The anti-MIF antibody may be administered once, but more preferably is administered multiple times. For example, the antibody may be administered from three times daily to once every six months or longer. The administering may be on a schedule such as three times daily, twice daily, once daily, once every two days, once every three days, once weekly, once every two weeks, once every month, once every two months, once every three months and once every six months.

The invention also encompass the use of an anti-MIF antibody or antigen-binding fragment thereof, in the manufacture of a medicament for the treatment of immunological diseases such as inflammatory diseases and hyperproliferative disorders.

The invention further encompass an anti-MIF antibody or antigen-binding fragment thereof, for use in treating immunological diseases such as inflammatory diseases and hyperproliferative disorders.

The invention also encompass an anti-MIF antibody or antigen-binding fragment thereof, for use in diagnostic methods. In one embodiment the anti-MIF antibody or antigen-binding portion thereof can be used to detect human MIF in a biological sample.

The anti-MIF antibodies or the antigen-binding portions thereof can also be used to determine the level of cell surface MIF in a tissue or in cells derived from the tissue. In some embodiments, the tissue is diseased tissue. The tissue can then be used in an immunoassay to determine, e.g., total MIF levels, cell surface levels of MIF, or localization of MIF.

The invention further relates to kits comprising an anti-MIF antibody or an antigen-binding portion of the invention or a pharmaceutical composition comprising such an antibody or portion. A kit may include, in addition to the antibody or pharmaceutical composition, diagnostic or therapeutic agents. A kit also can include instructions for use in a diagnostic or therapeutic method.

The invention further relates to a process for the identification of anti-MIF antibodies capable of inhibiting human MIF biological function and inducing a beneficial effect in an animal model by carrying out the following steps:

a) selecting an antibody that binds to active MIF and does not bind to non-active MIF
b) testing said antibody in in-vitro assays, such as glucocorticoid overriding (GCO) assay, or cell proliferation assays
c) selecting an antibody, which inhibits GCO and/or cell proliferation.

Results have shown that an anti-MIF antibody that only binds active MIF and does not bind non-active MIF and further inhibits GCO and/or cell proliferation induces a beneficial effect in an animal model (e.g. Example 6)

The present invention will be further illustrated by following examples, without any limitation thereto.

EXAMPLES

Example 1

Antibody Selection

Phage display technology is used to generate human anti-MIF antibody fragments. Starting from a phage display library, different screening campaigns are performed, three of them by using full length MIF (human MIF coated/human MIF in solution/human-murine MIF alternating). The others by using six MIF derived peptides alternating with full length MIF. These six peptides are designed by dividing the MIF protein into six peptides of approximately 30 amino acids with overlapping stretches of approximately 15-amino acids. After several selection rounds unique binders are identified, all unique binders are expressed and purified as human IgG4 antibodies. These antibodies are tested in several assays to demonstrate the in-vitro inhibition of MIF. An epitope mapping to determine the binding region within the MIF protein is carried. 193 antibodies are tested and categorized according to their in-vitro activity of inhibiting MIF. In-vitro assays are described below. Three murine anti-MIF antibodies are used as control (III.D.9, XIV.14.3 and XIV.15.5).

Example 2

Inhibition of Glucocorticoid Overriding Activity of MIF (GCO)

This method is based on the inhibition of endogenous MIF, i.e. MIF that is produced by the cell line used. This method is applied for antibody screening and for determination of dose response curves.

GCO-Assay for Antibody Screening:

A THP1 suspension culture is centrifuged and cells are resuspended in fresh full medium to a cell density of $10^6$ cells per ml. This culture is transferred into wells of a 96-well microplate (90 µl/well) and anti-MIF antibody is added to give a final concentration of 75 µg/ml. Each antibody is tested in triplicate. After o/n incubation at 37° C. dexamethasone is added to give a concentration of 2 nM and after one hour incubation at 37° C. LPS is added (3 ng/ml final concentration). After further six hours incubation at 37° C. the supernatant is harvested and the IL-6 concentrations are determined in an ELISA (Cytoset kit, commercially available). The results of the triplicates are averaged and the percentage of IL-6 secretion is determined in comparison to the control antibodies. Antibodies that result in an IL-6 secretion of less than 75% are evaluated as positive.

Assay for Determination of IC50 Values

The experimental procedure is carried out as described for the screening assay with the exception that increasing amounts of antibody are used (typically from 1-125 nM). The resultant dose response curve is expressed as % inhibition in comparison to a negative control antibody. This curve is used for calculation of the maximum inhibitory effect of the antibody (% Inh max) and the antibody concentration that shows 50% of the maximum inhibitory effect (IC50)

Results are summarized in FIG. 8, column 3 (IC50) and column 4 (maximum inhibition). For comparison, murine antibody XIV.14.3 shows 36% inhibition of GCO only (data not shown).

Example 3

Inhibition of Cell Proliferation

Serum stimulates secretion of MIF in quiescent NIH/3T3 and MIF in turn stimulates cell proliferation. Antibodies inhibiting this endogenous MIF, therefore, decrease the proliferation of quiescent NIH/3T3 cells. The reduction of proliferation is determined by the incorporation of $^3$H-thymidine.

1000 NIH/3T3 cells per well are incubated in a 96 well plate over the weekend at 37° C. in medium containing 10% serum. Cells are then starved over night at 37° C. by incubation in medium containing 0.5% serum. The 0.5% medium is removed and replaced by fresh medium containing 10% serum, 75 µg/ml antibody and 5 µCi/ml of 3H-Thymidine. After 16 hours incubation in a $CO_2$ incubator at 37° C. cells are washed twice with 150 µl of cold PBS per well. Using a multi-channel pipette 150 µl of a 5% (w/v) TCA solution per well are added and incubated for 30 minutes at 4° C. Plates are washed with 150 µl PBS. Per well 75 µl of a 0.5M NaOH solution with 0.5% SDS are added, mixed and stored at room temperature. Samples are measured in a β-counter by mixing 5 ml of Ultima Gold (Packard) and 75 µl sample solution. Each determination is done in triplicate and the values are compared with the values of the control antibody by a t-test. Antibodies that significantly reduce proliferation ($P<0.05$) are evaluated as positive. Results are summarized in FIG. 8, column 5.

Example 4

Binding Studies: Epitope Determination of Anti-MIF Antibodies

Each peptide is diluted in coupling buffer to give a peptide concentration of typically 5 µg/ml, is added to microplates (NUNC Immobilizer™ Amino Plate F96 Clear) and incubated over night at 4° C. (100 µl/well). As controls recombinant full length MIF and PBS are used. The plate is washed 3 times with 200 µl PBST and antibodies (4 µg/ml in PBS) are added (100 µl/well) and incubated for 2 hours at room temperature with gentle shaking. The plate is washed 3 times with 200 µl PBST and detection antibody (e.g. Fc specific anti-human IgG/HRP labeled, Sigma) is added (100 µl/well). After incubation for 1 hour at room temperature with gentle shaking the plate is washed 3 times with 200 µl PBST. Each well is incubated with 100 µl TMB solution (T-0440, Sigma) for 30 minutes in the dark. Staining reaction is stopped by adding 100 µl of 1.8 M $H_2SO_4$-solution per well. Samples are measured at 450 nm.

Example 5

Competition of Human Anti-MIF Antibodies with Murine Anti-MIF Antibody III.D.9

Antibody Bax94 is used for competition with mouse anti MIF antibodies III.D.9. 96 well plates (NUNC Maxisorp) are coated with recombinant human MIF. The murine anti-MIF antibody II.D.9 and human anti-MIF antibodies are diluted in TBST/2% BSA and mixed, whereas the final concentration of III.D9 is kept at 2 µg/ml and the concentration of human anti-MIF antibodies is increased from 0 µg/ml to typically 32 µg/ml. After washing of the microplate the antibodies are applied and incubated at room temperature for typically 2 hours. After washing, the plate is incubated with anti Mouse IgG (Fc spec.) peroxidase conjugate and incubated for 1 hour at room temperature. After washing, the plate is incubated with TMB-solution and the staining reaction is stopped by adding $H_2SO_4$-solution. Fitting of the resultant competition curve enables the calculation of the maximum inhibition of the III.D.9 binding. The results are summarized in FIG. 8, column 6.

Example 6

Figure 6:
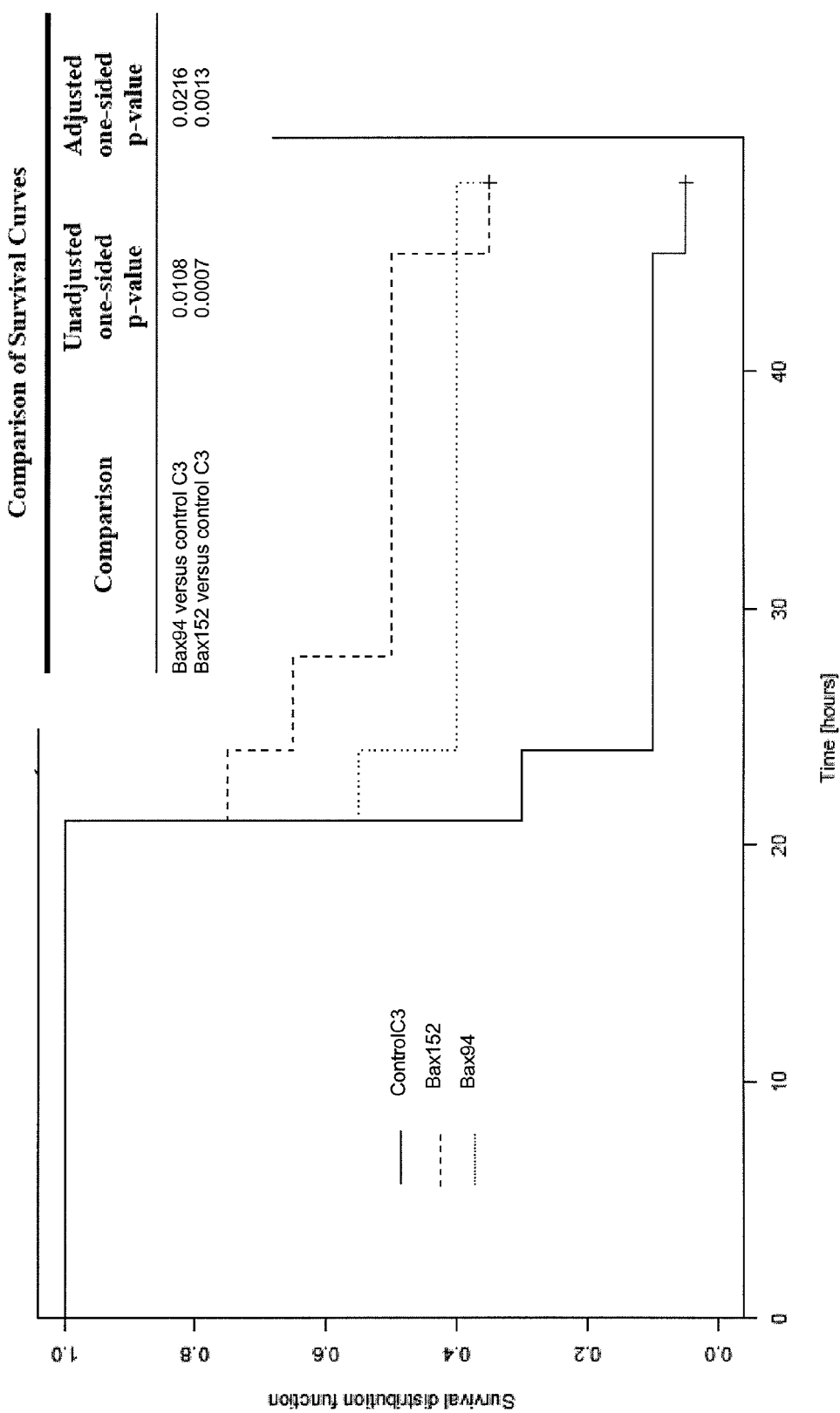
FIG. 6: Antibody Bax94 (dotted line) and antibody Bax152 (dashed line) showed increased survival and delayed time to death in the peritonitis animal model compared with a control antibody (C3).

Increased Survival of Anti-MIF Antibodies in the Live *E. coli* Peritonitis Animal Model The experiments are carried out according to Calandra et al. (Nature Immunology, 2000) using female NMRI mice (25-30 g, 6-10 weeks of age) that are injected intraperitoneally with 6000 CFU of an *E. coli* 0111:B4 suspension in 15% mucin and 4% hemoglobin. Two or three colonies (*E. coli* 0111:B04) from a nutrient agar plate culture are inoculated into 10 ml of TSB and incubated overnight at 36° C. with shaking. The culture is diluted in physiological saline to the required concentration(s)—an overnight the culture typically reaches $2*10^9$ CFU/ml—and mixed with mucin and hemoglobin (1 volume of diluted inoculum, 2 volumes of 15% mucin, 2 volumes of 4% hemoglobin). As the inoculum mixture tends to sediment out, it is mixed between injections. A large (e.g. 23 gauge) needle is used for injections to avoid blockage of the needle by particulates in the injection mixture. Antibody Bax94 (IgG4) and an isotype matching control antibody are given 2 hours prior to bacterial challenge interperitoneally. The antibody dosage is typically 800 µg/mouse and 20 mice are used for each group. A statistically significant effect on survival/time to death could be shown for the IgG1 and IgG4 isotypes of human anti-MIF antibodies. FIG. 6 shows the results obtained for antibody Bax94 and antibody Bax152 (IgG4). Kaplan-Meier statistics is used for evaluation of the survival curves.

Example 7

Binding Specificity for Active MIF

The anti-MIF antibodies described in this invention are able to discriminate between active and non-active MIF, which are generated by mild oxidation or reduction, respectively. Discrimination between these conformers is assessed by ELISA or surface plasmon resonance.

ELISA for Assessing Differential Binding of the Antibodies:
Transformation of MIF into its active conformation by mild oxidation. Recombinant human MIF (0.5 mg/ml in PBS) is incubated for 3 h at 37° C. with a 3-fold excess (volume) of a saturated solution of L-Cystine in PBS (~0.4-0.5 mM L-Cystine). The MIF is then dialyzed two times against PBS in a Slide-A-Lyzer® Dialysis Cassette with a molecular-weight cutoff of 7 kDa (Pierce).
Transformation of MIF into its non-active conformation. MIF is reduced at a concentration of 0.5 mg/ml by overnight incubation with 8-16 mM dithiothreitol (final concentration) at 4° C.

Figure 7:
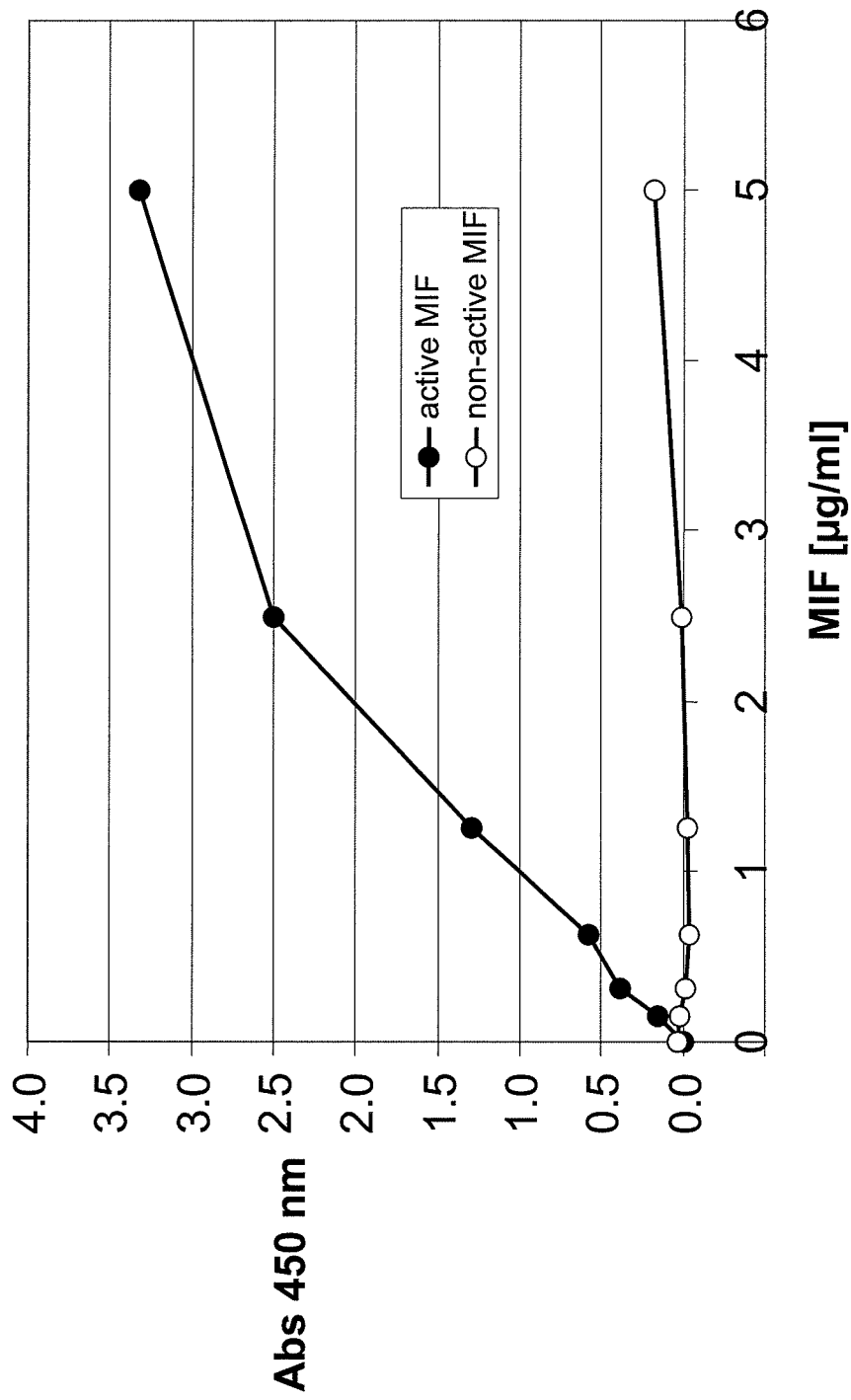
FIG. 7: Differential binding of antibody Bax94 to active MIF and non-active MIF. Antibody Bax94 binds active MIF in a direct ELISA format, whereas non-active-MIF does not bind.

ELISA Protocol.
The anti-MIF antibodies are coated into 96-well microplates (NUNC Maxisorp™) at a concentration of 5 µg/ml (dilution in coating buffer). After washing the plate with TBST (Tris-buffered saline with 0.1% Tween-20 (v/v)) and blocking with TBST/2% BSA (TBST and 2% bovine serum albumin (w/v)), dilution series of either active or non-active MIF are added and incubated at room temperature for 1-2 h. Bound MIF is detected using a polyclonal rabbit anti-MIF antibody and a horseradish peroxidase labeled goat-anti-rabbit antibody (Biorad). TBST/2% BSA is used to dilute MIF, the rabbit anti-MIF antibody and the peroxidase conjugate to reduce unspecific binding. FIG. 7 shows the ELISA results obtained with antibody Bax94.

Assessing Differential Binding of the Antibodies by Biacore.
Binding kinetics of active and non-active MIF to antibody Bax94 are examined by surface plasmon resonance analysis using a Biacore 3000 System. Therefore, 10000 Response Units of Bax94 are immobilized on a sensor chip with a CM5 (=carboxymethylated dextran) matrix and incubated with active or non-active MIF huMIF in pro-reductive and pro-oxidative Glutathione redox buffers, ranging from 4.8 mM GSH/0.2 mM GSSG (GSSG=oxidized Glutathione) to 5 mM GSSG in HBS-EP buffer (GE Healthcare). As a control, MIF is used for binding analysis in a second flow cell containing an immobilized isotype control antibody. Binding response units of control antibody and antibody Bax94 are subtracted for evaluation.

Example 8

Detection of Active MIF on the Surface of THP-1 Cells

Cells are incubated with anti-MIF antibody Bax94. Cells are washed with ice cold PBS and resuspended in cold cell lysis buffer (Cell Signaling Technology®). Magnetic Protein G Dynabeads® (Invitrogen) are blocked with TBST+5% nonfat dried milk (w/v), washed and added to the lysed cells. Immunoprecipitation is carried out at 4° C. overnight. The beads are then washed with cell lysis buffer and TBST and boiled in SDS PAGE sample buffer (without reducing agents). Samples are subjected to non-reductive SDS PAGE for Western Blot analysis.

Example 9

Binding of Anti-MIF Antibodies to Membrane Bound MIF

THP-1 cells are washed with ice cold PBS and resuspended in cold cell staining buffer (Biolegend) supplemented with 200 µg/ml mouse IgG. FITC- or TRITC-labeled anti-MIF antibodies are added to give a final concentration of typically 200-500 nM and incubation is done at 4° C. Cells are subsequently washed with ice cold cell staining buffer and resuspended in cell staining buffer supplemented with the Via-Probe™ Cell Viability Solution (BD Biosciences). Cells are measured in an FACS Canto™ II Flow Cytometry System (BD Biosciences) and the median FITC-/TRITC-shift of the viable cell populations are compared with the Dye-labeled isotype control antibody.

Example 10

Affinity Determination of Fab Fragments of Anti-MIF Antibodies by Biacore

Typically 40 RU Units of human recombinant MIF are immobilized on a sensor chip with a CM5 (=carboxymethylated dextran) matrix (Biacore). Fab fragments are injected at a concentration range of typically 6-100 nM diluted in HBS-EP. After each cycle the chip is regenerated with 50 mM NaOH+1M NaCl. Affinities are calculated according to the 1:1 Langmuir model. The results are summarized in FIG. 8, column 7.

Example 11

Beneficial Effect of Anti-MIF Antibodies in an Animal Model for Crescentic Glomerulonephritis The anti-MIF antibodies are tested in a rat model of crescentic glomerulonephritis described by Frederick W. K. Tam et. al. (Nephrol Dial Transplant, 1999, 1658-1666).

Nephrotoxic nephritis is induced in male Wistar Kyoto rats by a single intravenous injection of anti-rat glomerular basement membrane serum. In the preventive setup of the experiment treatment with anti-MIF antibodies and an isotype matching control antibody is started at the time of induction of nephritis (day 0) by interperitoneal injection of the antibody. Treatment is typically repeated every second day and animals are culled on day 7 for histological analyses. Urine is collected prior to the experiment (baseline) and on prior to the termination of the experiment (day 7). In a therapeutic setup, treatment with anti MIF antibody is started 4 days after induction of disease and repeated every second day. Rats are typically culled on day 8. Urine is collected prior to the experiment (baseline), prior to start of treatment (day 4) and prior to culling of the animals (day 8). Antibody dosage is typically 1-20 mg/kg per injection and 6 to 8 rats are used for each group. Disease severity is determined by measuring proteinuria, macrophage infiltration into the glomerulus and histological damage (crescent formation). In a preventive experiment treatment with anti-MIF antibody Bax69 (10 mg/kg per dose) for 7 days results in a 47% reduction of proteinuria in comparison to control antibody treated animals. Treatment of established disease (therapeutic experiment) results in a dose dependent reduction of proteinuria by 16% (10 mg/kg Bax69 per dose) and 34% (20 mg/kg Bax69 per dose) in comparison to control antibody treated animals.

Example 12

Beneficial Effect of Anti-MIF Antibodies in an Animal Model for Ulcerative Colitis (Adoptive Transfer of Naïve T cells in Rag −/− Mice)

C57BL/6 mice were sacrificed and CD45RBhi cells (naïve T cells) are isolated by FACS sorting of the spleen cell population. CD45RBhi cells ($5\times10^5$) are injected i.p. in Rag−/− C57BL/6 mice (7-9 weeks old), which develop of Ulcerative colitis after approx. 2 weeks. (de Jong et al., Nature immunology., 2001, 1061-1066). Anti-MIF antibodies and the isotype control antibody are injected intraperitoneally twice a week (1 mg/mouse/dose). In a preventive setup treatment is started at the time of injection of T-cells. In a therapeutic setup, treatment is started 4 weeks after induction of the disease. Mice are monitored weekly for weight and disease development. Typically eight weeks after the transfer of CD4CD45RBhi cells into Rag−/− C57BL/6 recipients the disease activity index (DAI) is calculated and colon sections are collected for histology index (HI) score. Diseases activity index (DAI) and histology index (HI) are determined at the end of the animal model (DAI is based on four parameters: hunching and wasting (scored 0 or 1), colon thickening (0-3) and stool consistency (0-3)). In a therapeutic experiment anti-MIF antibodies Bax69 and BaxA10 are used for treatment of established disease and the mean DAI is significantly reduced by approx. 60% (Bax69) and approx 40% (BaxA10) in comparison to isotype control treated mice. Furthermore, the mean HI score is reduced by approximately 33% after treatment with Bax69.

Example 13

Beneficial Effect of Anti-MIF Antibodies in an Animal Model for Ulcerative Colitis (Agonistic Anti-CD40 Model)

This model is based on the activation of macrophages and dendritic cells by an agonistic anti-CD40 antibody, which induces intestinal pathology that resembles IBD in Rag1−/− mice.

Age/sex matched Rag-1 −/− mice (4-5 wks) are purchased form Jackson Laboratories and kept for two weeks prior to the experiment in the animal facility. The agonist-CD40 monoclonal antibody (FGK45, IgG2a) or Isotype control Rat IgG2a are dissolved in PBS at 1 mg/ml. Five groups (10 mice each group) are injected i.p with 200 µg of agonist anti-CD40 monoclonal antibody and out of that four groups are treated with anti-MIF antibodies on day 0 and day 1 (2×1 mg/mouse). The sixth group (10 mice) is injected only with isotype control (Rat IgG2a, healthy control). Mice are weighed for the next 7 days. On Day 7, disease activity index (DAI) was calculated and colon sections collected for histology index (HI) score. The DAI score is based on: hunching (0-1); wasting (0-1), stool consistency (0-3) and colon thickening (0-3). Histology score was based on thickness (0-3), crypt elongation, inflammation (0-3) and abscess (0-1). Treatment with anti-MIF antibodies Bax94, BaxA10 and Bax69 significantly reduces the DAI score (BaxA10:~48% reduction; Bax94~62% reduction; Bax69~73% reduction) compared to isotype control treated mice. Furthermore, the mean HI scores is also reduced by the these antibodies.

Example 14

Inhibition of Tumor Growth in Mf1 Nude Mice by Anti MIF Antibodies

Human prostate adenocarcinoma cells (PC-3) are harvested from exponentially growing cultures and mixed with growth factor-depleted matrigel. $2*10^6$ cells in 0.25 ml matrigel are inoculated subcutaneously into the right flank of Mf1 nude mice. Treatment with anti-MIF antibody Bax94 and the isotype control C3 is started one day after inoculation (0.6 mg antibody/mouse/day) and is repeated every second day. Measurement of the sizes of the tumors is typically started two weeks after cell injection and done every second day. The volumes are calculated using the formula $V=0.5*a*b^2$ (where "a" is the longest diameter and "b" is the shortest diameter). Tumor growth of mice treated with Bax94 is significantly reduced and the mean volume of the tumors analyzed 28 days after tumor induction is 4.3 fold higher within the isotype control treated group in comparison to the Bax94 treated group.

In a therapeutic setup of the experiment antibody treatment was started one week after tumor engraftment. 50 mg/kg per dose of the isotype control antibody C3 and the anti-MIF antibody Bax69 are injected intraperitoneally every second day. After 22 days of treatment the median of the tumor volume was determined to be 2.7 fold higher within the C3 treated group in comparison to the of Bax69 treated group.

Example 15

Pro-Apoptotic Effects of Anti-MIF Antibodies

Figure 9:
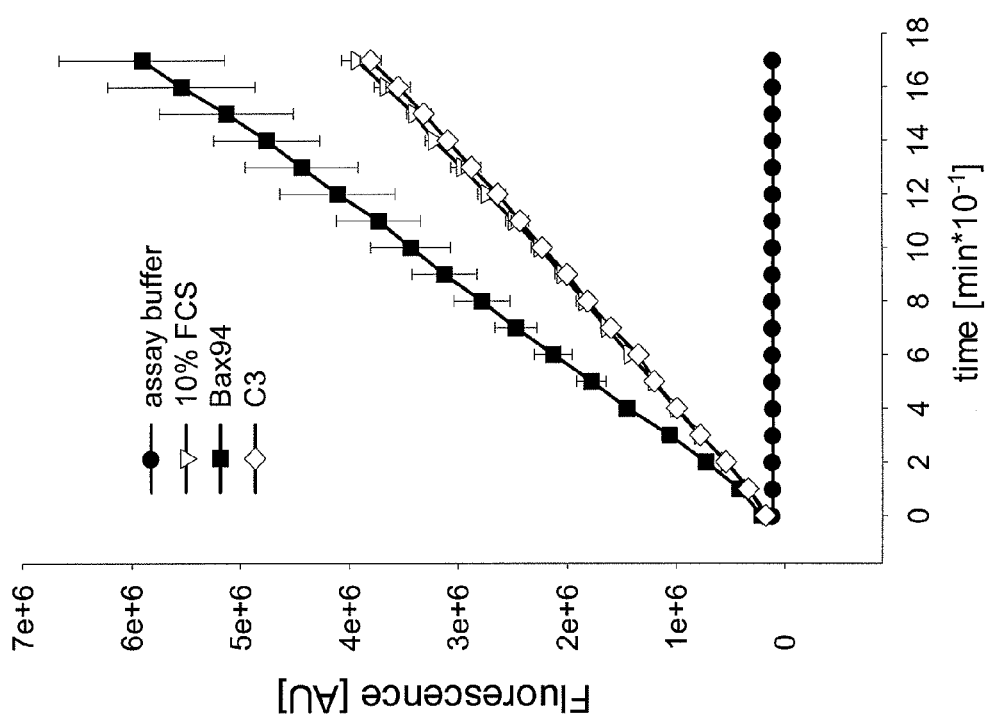
FIG. 9: Pro-apoptotic effects of anti-MIF antibodies in a cell based assay. Cellular caspase-3 (effector caspase) activities are shown after antibody treatment of PC-3 cells. Assays are done in triplicate and data are presented as mean±SD.

Pro-apoptotic effects of anti-MIF antibody Bax94 are shown in a cell based caspase-3 assay using the human prostate cancer cell line PC-3. PC-3 cells are seeded on 10 cm culture dishes (~10⁶ cells/dish) in the presence of 10% FCS. Fresh medium containing 100 nM antibody Bax94 or 100 nM control antibody C3 is added after 24 h. After another incubation period of 48 h cellular lysates are prepared and caspase-3 activity is measured by adding a fluorescent labeled caspase substrate. (FIG. 9).

Example 16

Inhibition of Tumor Cell Invasion

Anti MIF antibodies Bax94 and Bax69 are tested in Transwell™ invasion assays, using the human prostate cancer cell line PC-3.

Figure 10:
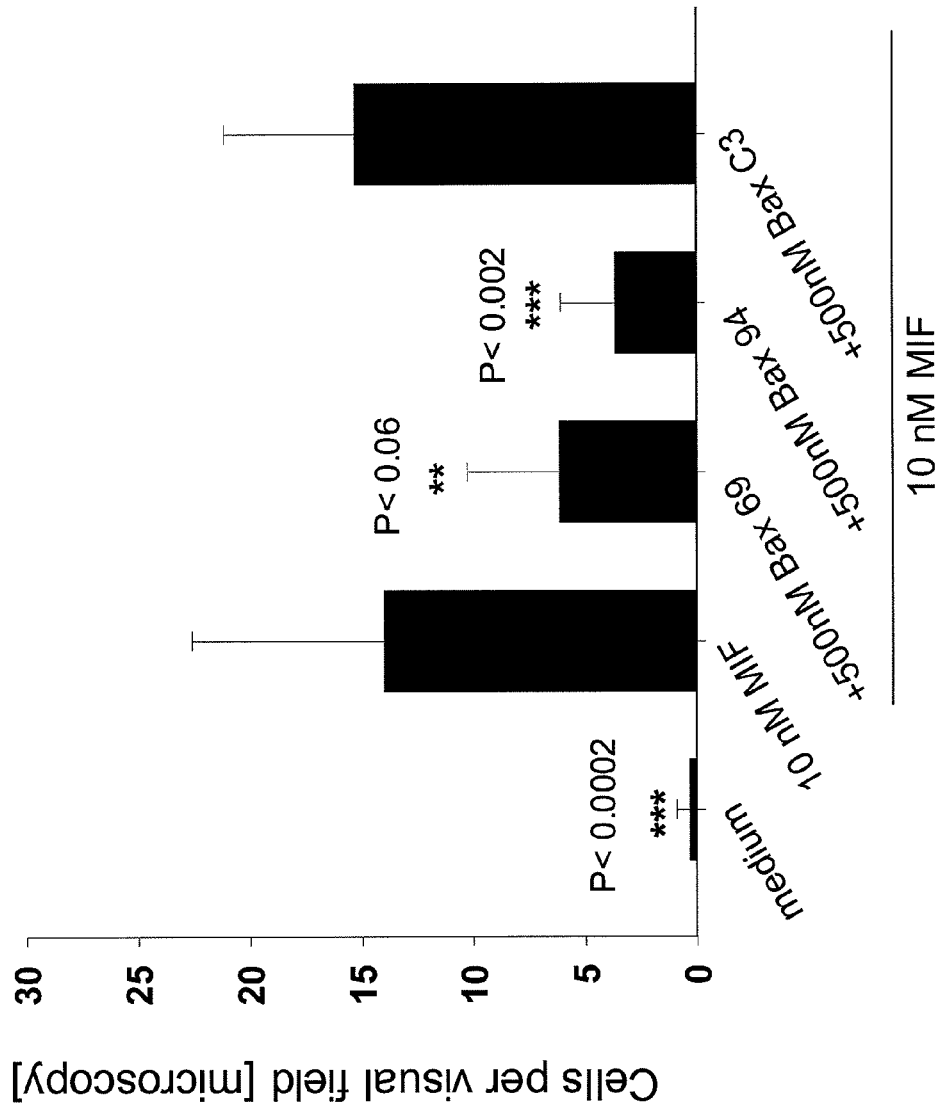
FIG. 10: Anti-invasive effects of anti-MIF antibodies. The invasion of PC-3 prostate cancer cells through pores of matrigel-coated Transwell™ inserts is examined. The number of invaded cells per visual field are counted (microscopy at 400 fold magnification). Data are presented as mean±SD from 3-10 visual field counts and significant differences are shown.

$5*10^4$ PC-3 cells are seeded per well in 24 well-Transwell™ dishes (8 μm pore size), which are coated with polyD-lysine on the bottom face of the polycarbonate membrane and with growth-factor depleted matrigel on the Transwell™ insert surface. Cells are allowed to attach for 4 h in the presence of 10% FCS. Thereafter, the medium was changed to serum-free medium and cells are starved overnight (i.e. for 16 h). Subsequently, compounds (10 nM MIF, 500 nM antibodies) are added to the lower chamber. Cells are allowed to migrate through the porous membrane for 24 h. After this incubation period, attached migrated cells of the lower face of the membrane are stained with Giemsa solution. The number of cells adhering to the lower face of the membrane is counted in independent visual fields at 400-fold magnification (FIG. 10).

The invention claimed is:

1. A monoclonal antibody or an antigen-binding portion thereof that specifically binds to the C-terminal region, said C-terminal region spanning aa 50-68, or the center region, said center region spanning aa 86-102, of human macrophage inhibitory factor (MIF) and inhibits human MIF biological function.

2. The monoclonal antibody or antigen-binding portion according to claim 1, wherein said antibody or antigen-binding portion possesses at least one of the following properties:
   a) inhibits glucocorticoid overriding (GCO) activity;
   b) inhibits proliferation of cancer cells or fibroblasts;
   c) binds to active MIF;
   d) does not bind to non-active MIF.

3. The monoclonal antibody or antigen-binding portion according to claim 1, wherein said antibody or antigen-binding portion binds human MIF with a $K_D$ less than 500 nM.

4. The monoclonal antibody or antigen-binding portion according to claim 1, wherein said antibody or said antigen-binding portion binds to active MIF.

5. The monoclonal antibody according to claim 1, wherein said antibody is selected from the group consisting of:
   antibody Bax69, defined as having a $V_L$ region comprising a nucleic acid sequence of SEQ ID NO:14 and a $V_H$ region comprising a nucleic acid sequence of SEQ ID NO:20;
   antibody Bax94, defined as having a $V_L$ region comprising a nucleic acid sequence of SEQ ID NO:16 and a $V_H$ region comprising a nucleic acid sequence of SEQ ID NO:22;
   antibody Bax152, defined as having a $V_L$ region comprising a nucleic acid sequence of SEQ ID NO:17 and a $V_H$ region comprising a nucleic acid sequence of SEQ ID NO:23; and
   antibody BaxA10, defined as having a $V_L$ region comprising a nucleic acid sequence of SEQ ID NO:18 and a $V_H$ region comprising a nucleic acid sequence of SEQ ID NO:24.

6. The monoclonal antibody according to claim 1, wherein said antibody is an IgG4 antibody having a single mutation, whereby a-CPSC (SEQ ID NO:25) sub-sequence in the Fc region of IgG4 is changed to -CPPC (SEQ ID NO: 26).

7. The monoclonal antibody or the antigen-binding portion according to claim 1, for use in treating an immunological disease, wherein said immunological disease is an inflammatory disease or a hyperproliferative disorder.

8. A pharmaceutical composition, comprising the monoclonal antibody or the antigen-binding portion according to claim 1 and a pharmaceutically acceptable carrier.

9. A method for treating an immunological disease in a subject, including a human, comprising the step of administering to said subject in need thereof a therapeutically effective amount of the monoclonal antibody or the antigen-binding portion according to claim 1, wherein said antibody or said antigen binding portion further inhibits human MIF biological function;
   wherein the immunological disease is selected from a group consisting of peritonitis, crescentic glomerulonephritis, and ulcerative colitis.

10. An isolated cell line that produces the monoclonal antibody or the antigen-binding portion according to claim 1.

11. An isolated nucleic acid molecule comprising a nucleotide sequence that encodes the heavy chain, or the light chain, of the monoclonal antibody or the antigen-binding portion according to claim 1.

12. A vector comprising the nucleic acid molecule according to claim 11, wherein the vector comprises an expression control sequence operably linked to said nucleic acid molecule.

13. A host cell comprising the nucleic acid molecule according to claim 11.

14. A host cell comprising a nucleic acid molecule encoding the heavy chain and a nucleic acid molecule encoding the light chain of the monoclonal antibody or the antigen-binding portion according to claim 1.

15. A method of producing a monoclonal antibody or an antigen-binding portion thereof, comprising culturing the host cell according to claim 14 under suitable conditions and recovering said antibody or antigen-binding portion thereof.

16. The monoclonal antibody or the antigen-binding portion according to claim 7, wherein said inflammatory disease is selected from the group consisting of crescentic glomerulonephritis, ulcerative colitis, and peritonitis.

17. A host cell comprising the vector according to claim 12.

* * * * *